(12) United States Patent
Kiechl et al.

(10) Patent No.: US 7,153,679 B2
(45) Date of Patent: Dec. 26, 2006

(54) MARBURG I MUTANT OF FACTOR VII ACTIVATING PROTEASE (FSAP) AS RISK FACTOR FOR ARTERIAL THROMBOSIS

(75) Inventors: Stefan Kiechl, Zirl (AT); Johann Willeit, Innsbruck (AT); Christian Josef Wiedermann, Innsbruck (AT); Juergen Roemisch, Voesendorf (AT); Thomas Weimer, Gladenbach (DE); Annette Feussner, Marburg (DE); Hans-Arnold Stoehr, Wetter (DE); Volker Doersam, Marburg (DE); Wiegand Lang, Cölbe (DE); Margret Becker, Marburg (DE); Claudia Nerlich, Marburg (DE); Gudrun Muth-Naumann, Wetter (DE); Bernd Knoblauch, Lich (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 10/391,215

(22) Filed: Mar. 19, 2003

(65) Prior Publication Data

US 2004/0009543 A1    Jan. 15, 2004

Related U.S. Application Data

(63) Continuation-in-part of application No. 09/912,559, filed on Jul. 26, 2001, now Pat. No. 6,831,167.

(30) Foreign Application Priority Data

| Jul. 26, 2000 | (DE) | 100 36 641 |
| Oct. 10, 2000 | (DE) | 100 50 040 |
| Oct. 21, 2000 | (DE) | 100 52 319 |
| Apr. 12, 2001 | (DE) | 101 18 706 |
| Mar. 19, 2002 | (DE) | 102 12 246 |
| Aug. 16, 2002 | (DE) | 102 38 429 |

(51) Int. Cl.
C12N 9/64 (2006.01)
C12Q 1/68 (2006.01)
C12Q 1/37 (2006.01)

(52) U.S. Cl. .......................... 435/226; 435/6; 435/23; 435/24

(58) Field of Classification Search ................ 435/226, 435/6, 23, 24; 424/94.64
See application file for complete search history.

(56) References Cited

U.S. PATENT DOCUMENTS

| 5,175,087 A | 12/1992 | Ranby et al. |
| 5,968,759 A | 10/1999 | Romisch et al. |
| 2002/0110552 A1 | 8/2002 | Roemisch et al. |
| 2003/0077271 A1 | 4/2003 | Roemisch et al. |
| 2003/0124622 A1 | 7/2003 | Roemisch et al. ........... 435/7.4 |
| 2003/0215447 A1 | 11/2003 | Roemisch et al. |
| 2004/0063187 A1 | 4/2004 | Roemisch et al. |
| 2004/0186277 A1 | 9/2004 | Roemisch et al. |
| 2005/0032109 A1 | 2/2005 | Roemisch et al. |
| 2005/0202002 A1 | 9/2005 | Roemisch et al. |

FOREIGN PATENT DOCUMENTS

| DE | 199 26 531.3 | 6/1999 |
| DE | 199 03 693 A1 | 10/1999 |
| DE | 100 23 923 A1 | 12/2000 |
| DE | 199 37 218 A1 | 2/2001 |
| DE | 199 37 219 A1 | 2/2001 |
| DE | 100 36 641 | 2/2002 |
| EP | 0 952 215 A2 | 10/1999 |
| EP | 1 033 405 A2 | 9/2000 |
| EP | 1 059 359 A2 | 12/2000 |
| EP | 1 074 615 A1 | 2/2001 |
| EP | 1 074 616 A1 | 2/2001 |
| EP | 1 182 258 B1 | 2/2006 |

OTHER PUBLICATIONS

N.-H. Choi-Miura et al., "Proteolytic Activation and Inactivation of the Serine Protease Activity of Plasma Hyaluronan Binding Protein," *Biol. Pharm. Bull.*, 24(5):448-452 (2001).
J. Willeit et al., "Marburg I Polymorphism of Factor VII-Activating Protease: A Prominent Risk Predictor of Carotid Stenosis," *Circulation*, 107(5):667-670 (2003).
J. Römisch "Factor VII Activating Protease (FSAP): A Novel Protease in Hemostasis," *Biol. Chem.*, 383:1119-1124 (2002).
S. Kiechl & J. Willeit, "The Natural Course of Atherosclerosis. Part I: Incidence and Progression," *Arterioscler, Thromb. Vasc. Biol.*, 19:1484-90 (1999).
S. Kiechl & J. Willeit, "The Natural Course of Atherosclerosis. Part II: Vascular Remodeling," *Arterioscler. Thromb. Vasc. Biol.*, 19: 1491-8 (1999).
J. Willeit et al., "Distinct Risk Profiles of Early and Advanced Atherosclerosis. Prospective Results from the Bruneck Study," *Arterioscler. Thromb. Vasc. Biol.*, 20: 529-37 (2000).
S. Kiechl et al., "Chronic Infections and the Risk of Carotid Atherosclerosis. Prospective Results from a Large Population Study," *Circulation*, 103: 1064-70 (2001).
S. Kiechl et al., "Body Iron Stores and the Risk Carotid Atherosclerosis. Prospective Results from the Bruneck Study," *Circulation*, 96: 3300-7 (1997).
S. Kiechl et al., "Toll-like Receptor 4 Polymorphisms and Atherogenesis," *N. Engl. J. Med.*, 347: 185-92 (2002).
J. Römisch et al., "Quantitation of the Factor VII-and Single Chain Plasminogen Activator-Activating Protease in Plasmas of Healthy Subjects," *Blood Coagul. Fibrinolysis*, 12: 375-83 (2001).

(Continued)

*Primary Examiner*—Elizabeth Slobodyansky
(74) *Attorney, Agent, or Firm*—Finnegan, Henderson, Farabow, Garrett, Dunner, L.L.P.

(57) ABSTRACT

A novel arterial thrombosis risk factor comprising one or more of the identified mutants of coagulation factor VII-activating protease (FSAP) is described. In addition, diagnostic determination methods for detecting these mutants which are identified as risk factors are described.

20 Claims, 1 Drawing Sheet

OTHER PUBLICATIONS

Figure 1:
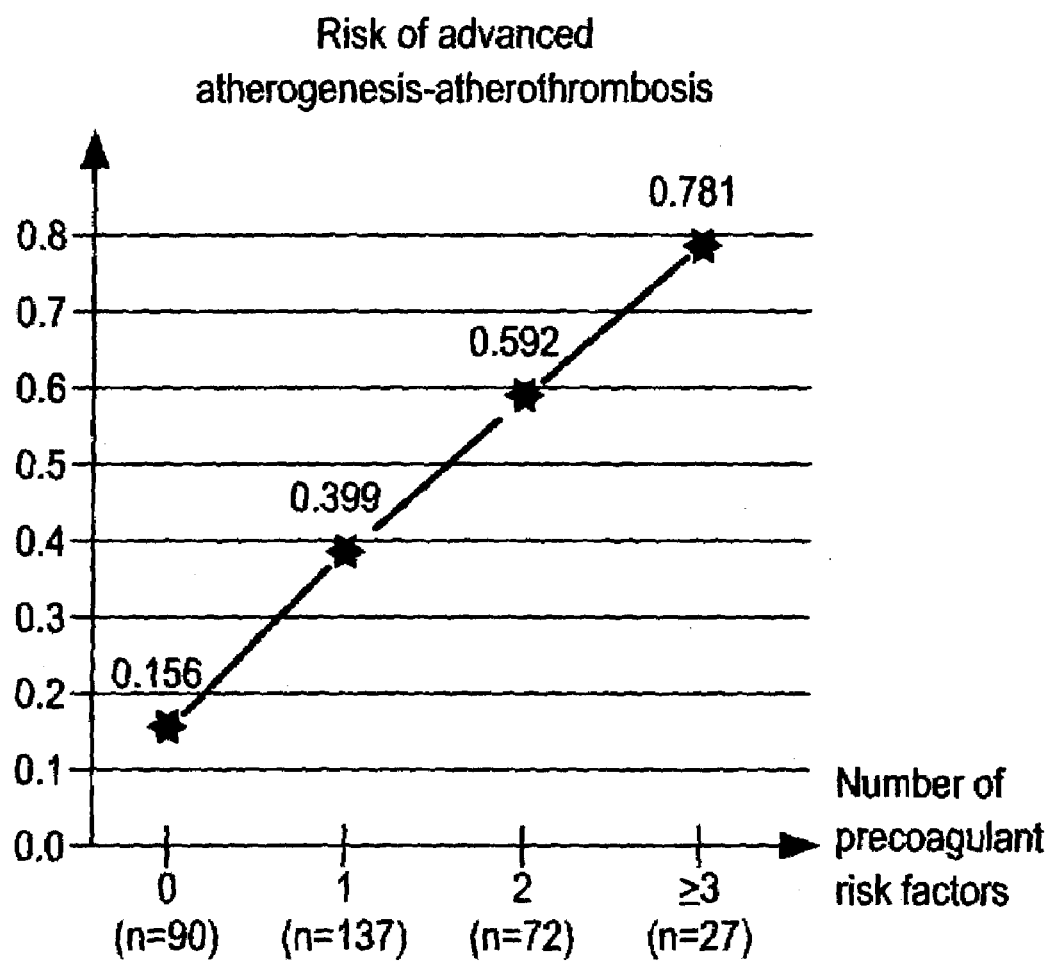

C. Kannemeier et al., "Factor VII and Single-Chain Plasminogen Activator-Activating Protease: Activation and Autoactivation of the Proenzyme," *Eur. J. Biochem.*, 268: 3789-96 (2001).

J. Roemisch et al., "The Frequent *Marburg I*Polymorphism Impairs the Pro-urokinase Activating Potency of the Factor VII-Activating Protease (FSAP)," *Blood Coagul. Fibrinolysis*, 13: 433-41 (2002).

T.C. Wilcosky & L.E. Chambless, "A Comparison of Direct Adjustment and Regression Adjustment of Epidemiologic Measures," *J. Chron. Dis.*, 38: 849-56 (1985).

N.H.- Choi-Miura, et al. "Purification and Characterization of a Novel Hyaluronan-Binding Protein (PHBP) from Human Plasma: It Has Three EGF, a Kringle and a Serine Protease Domain, Similar to Hepatocyte Growth Factor Activator"*J. Biochem.*, 119(6)1157-65 (1996).

A. Hunfeld, et al. "Identification of the Thrombin-Like Activity of PCCs"*Annals of Hematology*,(76 Suppl. 1):A101 (1998).

A. Hunfeld, et al. "Detection of a Novel Plasma Serine Protease During Purification of Vitamin K-dependent Coagulation Factors"*FEBS Letters*, 456:290-94 (1999).

J. Römisch, et al. "A Protease Isolated from Plasma which Activates FVII in a Tissue Factor Independent Manner but Inactivates FV and FVIII"*Annals of Hermatology*, (78 Suppl. 1):A10 (1999).

J. Römisch, et al. "The FVII Activating Protease Mediates Fibrinolytic Effects Activating Single-Chain Plasminogen Activators"*Annals of Hermatology*, (78 Suppl. 1):A24 (1999).

J. Römisch, et al. "A Protease Isolated from Human Plasma Activating Factor VII Independent of Tissue Factor"*Blood Coagul. Fibrinol.*, 10:471-479 (1999).

J. Römisch, et al. "The FVII Activating Protease Cleaves Single-Chain Plasminogen Activators"*Haemostasis*, (29):292-299 (1999).

T. Prins et al., "Cloning and characterization of a glutathione S-transferase homologue from the plant pathogenic fungus *Botrytis cinerea,*" *Molecular Plant Pathology*, 1: 169-178 (2000).

Doris, Pa, "Hypertension Genetics, Single Nucleotide Polymorphisms, and the Common Disease: Common Variant Hypothesis," *Hypertension*, 39(Part II): 323-331 (2002).

Stephens, JC et al., "Haplotype Variation and Linkage Disequilibrium in 313 Human Genes," *Science*, 293: 489-493 (2001).

Chakravarti, A., "Population Genetics—Making Sense out of Sequence," *Nature Genetics Supplement*, 21: 56-60 (1999).

Cargill, M. et al., "Characterization of Single-Nucleotide Polymorphisms in Coding Regions of Human Genes," *Nature Genetics*, 22: 231-238 (1999).

K. Laake et al., "Activation of Purified Plasma Factor VII By Human Plasmin, Plasma Kallikrein, And Activated Components of the Human Intrinsic Blood Coagulation System," *Thrombosis Research*, vol. 5 (6): 759-772 (1974).

K. Hashimoto et al., "Cloning of the cDNA for a Mouse Homologue of Human PHBP: A Novel Hyaturonan-Binding Protein," *Biol. Pharm. Bulletin*, vol. 20(11): 1127-1130 (1997).

J-I. Sumiya et al., "Isolation and Characterization of the Plasma Hyaturonan-Binding Protein (PHBP) Gene (HABP2)," *J. Biochem.*, vol. 122: 983-990 (1997).

M. Etscheid et al., "Characterization of a Novel Serine Protease From Plasma," (Abstract) (1999).

A. Vostrov et al., "Plasma Hyaturonan-binding Protein Is a Serine Protease," *J. Biological Chemistry*, vol. 275 (30): 22978-22985 (2000).

SEQUENCE LISTING

<160> NUMBER OF SEQ ID NOS: 8

<210> SEQ ID NO 1
<211> LENGTH: 1683
<212> TYPE: DNA
<213> ORGANISM: Homo sapiens

<400> SEQUENCE: 1

| | | | | | |
|---|---|---|---|---|---|
| atgtttgcca | ggatgtctga | tctccatgtt | ctgctgttaa | tggctctggt | gggaaagaca | 60 |
| gcctgtgggt | tctccctgat | gtctttattg | gaaagcctgg | acccagactg | gaccccctgac | 120 |
| cagtatgatt | acagctacga | ggattataat | caggaagaga | acaccagtag | cacacttacc | 180 |
| catgctgaga | tcctgactg | gtactacact | gaggaccaag | ctgatccatg | ccagcccaac | 240 |
| ccctgtgaac | acgtgggga | ctgcctcgtc | catgggagca | ccttcacatg | cagctgcctg | 300 |
| gctcctttct | ctgggaataa | gtgtcagaaa | gtgcaaaata | cgtgcaagga | caacccatgt | 360 |
| ggccggggcc | aatgtctcat | tacccagagt | cctccctact | accgctgtgt | ctgtaaacac | 420 |
| ccttacacag | gtcccagctg | ctcccaagtg | gttcctgtat | gcaggccaaa | ccctgccag | 480 |
| aatggggcta | cctgctcccg | gcataagcgg | agatccaagt | tcacctgtgc | ctgtcccgac | 540 |
| cagttcaagg | ggaaattctg | tgaaataggt | tctgatgact | gctatgttgg | cgatggctac | 600 |
| tcttaccgag | ggaaaatgaa | taggacagtc | aaccagcatg | cgtgccttta | ctggaactcc | 660 |
| cacctcctct | gcaggagaa | ttacaacatg | tttatggagg | atgctgaaac | ccatgggatt | 720 |
| ggggaacaca | atttctgcag | aaacccagat | gcggacgaaa | agccctggtg | ctttattaaa | 780 |
| gttaccaatg | acaaggtgaa | atgggaatac | tgtgatgtct | cagcctgctc | agcccaggac | 840 |
| gttgcctacc | agaggaaag | ccccactgag | ccatcaacca | agcttccggg | gtttgactcc | 900 |
| tgtggaaaga | ctgagatagc | agagaggaag | atcaagagaa | tctatggagg | ctttaagagc | 960 |
| acggcgggca | agcacccatg | gcaggcgtcc | ctccagtcct | cgctgcctct | gaccatctcc | 1020 |
| atgcccagg | gccacttctg | tggtggggcg | ctgatccacc | cctgctgggt | gctcactgct | 1080 |
| gcccactgca | ccgacataaa | aaccagacat | ctaaaggtgg | tgctagggga | ccaggacctg | 1140 |
| aagaaagaag | aatttcatga | gcagagcttt | agggtggaga | agatattcaa | gtacagccac | 1200 |
| tacaatgaaa | gagatgagat | tccccacaat | gatattgcat | tgctcaagtt | aaagccagtg | 1260 |
| gatggtcact | gtgctctaga | atccaaatac | gtgaagactg | tgtgcttgcc | tgatgggtcc | 1320 |
| tttcctctg | ggagtgagtg | ccacatctct | ggctggggtg | ttacagaaac | aggaaaaggg | 1380 |
| tcccgccagc | tcctggatgc | caaagtcaag | ctgattgcca | acactttgtg | caactcccgc | 1440 |
| caactctatg | accacatgat | tgatgacagt | atgatctgtg | caggaaatct | tcagaaacct | 1500 |
| gggcaagaca | cctgccaggg | tgactctgga | ggccccctga | cctgtgagaa | ggacggcacc | 1560 |
| tactacgtct | atgggatagt | gagctgggc | ctggagtgtg | gaagaggcc | agggtctac | 1620 |
| acccaagtta | ccaaattcct | gaattggatc | aaagccacca | tcaaaagtga | agtggcttc | 1680 |
| taa | | | | | | 1683 |

<210> SEQ ID NO 2
<211> LENGTH: 1683
<212> TYPE: DNA
<213> ORGANISM: Homo sapiens

<400> SEQUENCE: 2

| | | | | | |
|---|---|---|---|---|---|
| atgtttgcca | ggatgtctga | tctccatgtt | ctgctgttaa | tggctctggt | gggaaagaca | 60 |

```
gcctgtgggt tctccctgat gtctttattg gaaagcctgg acccagactg gaccccctgac    120 cagtatgatt acagctacga ggattataat caggaagaga acaccagtag cacacttacc    180
catgctgaga atcctgactg gtactacact gaggaccaag ctgatccatg ccagcccaac    240
ccctgtgaac acggtgggga ctgcctcgtc catgggagca ccttcacatg cagctgcctg    300
gctcctttct ctgggaataa gtgtcagaaa gtgcaaaata cgtgcaagga caacccatgt    360
ggccggggcc aatgtctcat tacccagagt cctccctact accgctgtgt ctgtaaacac    420
ccttacacag gtcccagctg ctcccaagtg gttcctgtat gcaggccaaa ccctgccag    480 aatgggcta cctgctcccg gcataagcgg agatccaagt tcacctgtgc ctgtcccgac    540
cagttcaagg ggaaattctg tgaaataggt tctgatgact gctatgttgg cgatggctac    600
tcttaccgag ggaaaatgaa taggacagtc aaccagcatg cgtgccttta ctggaactcc    660
cacctcctct gcaggagaa ttacaacatg tttatggagg atgctgaaac ccatgggatt    720
ggggaacaca atttctgcag aaacccagat gcggacgaaa agccctggtg ctttattaaa    780
gttaccaatg acaaggtgaa atgggaatac tgtgatgtct cagcctgctc agcccaggac    840
gttgcctacc agaggaaag ccccactgag ccatcaacca agcttccggg gtttgactcc    900
tgtggaaaga ctgagatagc agagaggaag atcaagagaa tctatggagg ctttaagagc    960
acggcgggca agcacccatg gcaggcgtcc ctccagtcct cgctgcctct gaccatctcc   1020
atgccccagg gccacttctg tggtggggcg ctgatccacc cctgctgggt gctcactgct   1080
gcccactgca ccgacataaa aaccagacat ctaaaggtgg tgctagggga ccaggacctg   1140
aagaaagaag aatttcatga gcagagcttt agggtggaga agatattcaa gtacagccac   1200
tacaatgaaa gagatgagat tccccacaat gatattgcat tgctcaagtt aaagccagtg   1260
gatggtcact gtgctctaga atccaaatac gtgaagactg tgtgcttgcc tgatgggtcc   1320 tttcctctg ggagtgagtg ccacatctct ggctggggtg ttacagaaac aggaaagggg   1380
tcccgccagc tcctggatgc caaagtcaag ctgattgcca acacttgtgt caactcccgc   1440
caactctatg accacatgat tgatgacagt atgatctgtg caggaaatct tcagaaacct   1500
gggcaagaca cctgccaggg tgactctgga ggccccctga cctgtgagaa ggacggcacc   1560
tactacgtct atgggatagt gagctggggc ctggagtgtg agaagaggcc aggggtctac   1620
acccaagtta ccaaattcct gaattggatc aaagccacca tcaaaagtga agtggcttc   1680 taa                                                                  1683

<210> SEQ ID NO 3
<211> LENGTH: 1683
<212> TYPE: DNA
<213> ORGANISM: Homo sapiens

<400> SEQUENCE: 3
atgtttgcca ggatgtctga tctccatgtt ctgctgttaa tggctctggt gggaaagaca     60
gcctgtgggt tctccctgat gtctttattg gaaagcctgg acccagactg gaccccctgac   120 cagtatgatt acagctacga ggattataat caggaagaga acaccagtag cacacttacc    180
catgctgaga atcctgactg gtactacact gaggaccaag ctgatccatg ccagcccaac    240
ccctgtgaac acggtgggga ctgcctcgtc catgggagca ccttcacatg cagctgcctg    300
gctcctttct ctgggaataa gtgtcagaaa gtgcaaaata cgtgcaagga caacccatgt    360
ggccggggcc aatgtctcat tacccagagt cctccctact accgctgtgt ctgtaaacac    420
```

```
ccttacacag gtcccagctg ctcccaagtg gttcctgtat gcaggccaaa cccctgccag    480 aatgggcta cctgctcccg gcataagcgg agatccaagt tcacctgtgc ctgtcccgac    540
cagttcaagg ggaaattctg tgaaataggt tctgatgact gctatgttgg cgatggctac    600
tcttaccgag ggaaaatgaa taggacagtc aaccagcatg cgtgccttta ctggaactcc    660
cacctcctct tgcaggagaa ttacaacatg tttatggagg atgctgaaac ccatgggatt    720
ggggaacaca atttctgcag aaacccagat gcggacgaaa agccctggtg ctttattaaa    780
gttaccaatg acaaggtgaa atgggaatac tgtgatgtct cagcctgctc agcccaggac    840
gttgcctacc cagaggaaag ccccactgag ccatcaacca gcttccgggt tttgactcc    900 tgtggaaaga ctgagatagc agagaggaag atcaagagaa tctatggagg ctttaagagc    960
acggcgggca agcacccatg gcaggcgtcc ctccagtcct cgctgcctct gaccatctcc   1020
atgccccagg gccacttctg tggtggggcg ctgatccacc cctgctgggt gctcactgct   1080
gcccactgca ccgacataaa aaccagacat ctaaaggtgg tgctagggga ccaggacctg   1140
aagaaagaag aatttcatga gcagagcttt agggtgcaga agatattcaa gtacagccac   1200
tacaatgaaa gagatgagat tccccacaat gatattgcat tgctcaagtt aaagccagtg   1260
gatggtcact gtgctctaga atccaaatac gtgaagactg tgtgcttgcc tgatgggtcc   1320 tttcctctg ggagtgagtg ccacatctct ggctggggtg ttacagaaac aggaaagggg   1380
tcccgccagc tcctggatgc caaagtcaag ctgattgcca acacttttgtg caactcccgc   1440 caactctatg accacatgat tgatgacagt atgatctgtg caggaaatct tcagaaacct   1500
gggcaagaca cctgccaggg tgactctgga ggccccctga cctgtgagaa ggacggcacc   1560
tactacgtct atgggatagt gagctggggc ctggagtgtg ggaagaggcc aggggtctac   1620
acccaagtta ccaaattcct gaattggatc aaagccacca tcaaaagtga aagtggcttc   1680
taa                                                                  1683
```

<210> SEQ ID NO 4
<211> LENGTH: 1683
<212> TYPE: DNA
<213> ORGANISM: Homo sapiens

<400> SEQUENCE: 4

```
atgtttgcca ggatgtctga tctccatgtt ctgctgttaa tggctctggt gggaaagaca     60
gcctgtgggt tctccctgat gtctttattg gaaagcctgg acccagactg gacccctgac    120
cagtatgatt acagctacga ggattataat caggaagaga acaccagtag cacacttacc    180
catgctgaga atcctgactg gtactacact gaggaccaag ctgatccatg ccagcccaac    240
ccctgtgaac acggtgggga ctgcctcgtc catgggagca ccttcacatg cagctgcctg    300
gctcctttct ctgggaataa gtgtcagaaa gtgcaaaata cgtgcaagga caacccatgt    360
ggccggggcc aatgtctcat tacccagagt cctcccctact accgctgtgt ctgtaaacac    420
ccttacacag gtcccagctg ctcccaagtg gttcctgtat gcaggccaaa cccctgccag    480 aatgggcta cctgctcccg gcataagcgg agatccaagt tcacctgtgc ctgtcccgac    540
cagttcaagg ggaaattctg tgaaataggt tctgatgact gctatgttgg cgatggctac    600
tcttaccgag ggaaaatgaa taggacagtc aaccagcatg cgtgccttta ctggaactcc    660
cacctcctct tgcaggagaa ttacaacatg tttatggagg atgctgaaac ccatgggatt    720
ggggaacaca atttctgcag aaacccagat gcggacgaaa agccctggtg ctttattaaa    780
gttaccaatg acaaggtgaa atgggaatac tgtgatgtct cagcctgctc agcccaggac    840
```

-continued

```
gttgcctacc cagaggaaag ccccactgag ccatcaacca agcttccggg gtttgactcc    900
tgtggaaaga ctgagatagc agagaggaag atcaagagaa tctatggagg ctttaagagc    960
acggcgggca agcacccatg gcaggcgtcc ctccagtcct cgctgcctct gaccatctcc   1020
atgccccagg gccacttctg tggtggggcg ctgatccacc cctgctgggt gctcactgct   1080
gcccactgca ccgacataaa aaccagacat ctaaaggtgg tgctagggga ccaggacctg   1140
aagaaagaag aatttcatga gcagagcttt agggtgcaga agatattcaa gtacagccac   1200
tacaatgaaa gagatgagat tccccacaat gatattgcat tgctcaagtt aaagccagtg   1260
gatggtcact gtgctctaga atccaaatac gtgaagactg tgtgcttgcc tgatgggtcc   1320
tttccctctg ggagtgagtg ccacatctct ggctggggtg ttacagaaac aggaaaaggg   1380
tcccgccagc tcctggatgc caaagtcaag ctgattgcca cactttgtgt caactcccgc   1440
caactctatg accacatgat tgatgacagt atgatctgtg caggaaatct tcagaaacct   1500
gggcaagaca cctgccaggg tgactctgga ggcccctga cctgtgagaa ggacggcacc   1560
tactacgtct atgggatagt gagctggggc ctggagtgtg agaagaggcc agggtctac   1620
acccaagtta ccaaattcct gaattggatc aaagccacca tcaaaagtga aagtggcttc   1680
taa                                                                 1683
```

<210> SEQ ID NO 5
<211> LENGTH: 560
<212> TYPE: PRT
<213> ORGANISM: Homo sapiens

<400> SEQUENCE: 5

```
Met Phe Ala Arg Met Ser Asp Leu His Val Leu Leu Met Ala Leu
  1               5                  10                  15

Val Gly Lys Thr Ala Cys Gly Phe Ser Leu Met Ser Leu Leu Glu Ser
                 20                  25                  30

Leu Asp Pro Asp Trp Thr Pro Asp Gln Tyr Asp Tyr Ser Tyr Glu Asp
             35                  40                  45

Tyr Asn Gln Glu Glu Asn Thr Ser Ser Thr Leu Thr His Ala Glu Asn
         50                  55                  60

Pro Asp Trp Tyr Tyr Thr Glu Asp Gln Ala Asp Pro Cys Gln Pro Asn
 65                  70                  75                  80

Pro Cys Glu His Gly Gly Asp Cys Leu Val His Gly Ser Thr Phe Thr
                 85                  90                  95

Cys Ser Cys Leu Ala Pro Phe Ser Gly Asn Lys Cys Gln Lys Val Gln
                100                 105                 110

Asn Thr Cys Lys Asp Asn Pro Cys Gly Arg Gly Gln Cys Leu Ile Thr
            115                 120                 125

Gln Ser Pro Pro Tyr Tyr Arg Cys Val Cys Lys His Pro Tyr Thr Gly
        130                 135                 140

Pro Ser Cys Ser Gln Val Val Pro Val Cys Arg Pro Asn Pro Cys Gln
145                 150                 155                 160

Asn Gly Ala Thr Cys Ser Arg His Lys Arg Arg Ser Lys Phe Thr Cys
                165                 170                 175

Ala Cys Pro Asp Gln Phe Lys Gly Lys Phe Cys Glu Ile Gly Ser Asp
            180                 185                 190

Asp Cys Tyr Val Gly Asp Gly Tyr Ser Tyr Arg Gly Lys Met Asn Arg
        195                 200                 205

Thr Val Asn Gln His Ala Cys Leu Tyr Trp Asn Ser His Leu Leu Leu
```

-continued

```
            210                 215                 220
Gln Glu Asn Tyr Asn Met Phe Met Glu Asp Ala Glu Thr His Gly Ile
225                 230                 235                 240

Gly Glu His Asn Phe Cys Arg Asn Pro Asp Ala Asp Glu Lys Pro Trp
                245                 250                 255

Cys Phe Ile Lys Val Thr Asn Asp Lys Val Lys Trp Glu Tyr Cys Asp
                260                 265                 270

Val Ser Ala Cys Ser Ala Gln Asp Val Ala Tyr Pro Glu Ser Pro
                275                 280                 285

Thr Glu Pro Ser Thr Lys Leu Pro Gly Phe Asp Ser Cys Gly Lys Thr
290                 295                 300

Glu Ile Ala Glu Arg Lys Ile Lys Arg Ile Tyr Gly Gly Phe Lys Ser
305                 310                 315                 320

Thr Ala Gly Lys His Pro Trp Gln Ala Ser Leu Gln Ser Ser Leu Pro
                325                 330                 335

Leu Thr Ile Ser Met Pro Gln Gly His Phe Cys Gly Gly Ala Leu Ile
                340                 345                 350

His Pro Cys Trp Val Leu Thr Ala Ala His Cys Thr Asp Ile Lys Thr
                355                 360                 365

Arg His Leu Lys Val Val Leu Gly Asp Gln Asp Leu Lys Lys Glu Glu
370                 375                 380

Phe His Glu Gln Ser Phe Arg Val Glu Lys Ile Phe Lys Tyr Ser His
385                 390                 395                 400

Tyr Asn Glu Arg Asp Glu Ile Pro His Asn Asp Ile Ala Leu Leu Lys
                405                 410                 415

Leu Lys Pro Val Asp Gly His Cys Ala Leu Glu Ser Lys Tyr Val Lys
                420                 425                 430

Thr Val Cys Leu Pro Asp Gly Ser Phe Pro Ser Gly Ser Glu Cys His
                435                 440                 445

Ile Ser Gly Trp Gly Val Thr Glu Thr Gly Lys Gly Ser Arg Gln Leu
450                 455                 460

Leu Asp Ala Lys Val Lys Leu Ile Ala Asn Thr Leu Cys Asn Ser Arg
465                 470                 475                 480

Gln Leu Tyr Asp His Met Ile Asp Asp Ser Met Ile Cys Ala Gly Asn
                485                 490                 495

Leu Gln Lys Pro Gly Gln Asp Thr Cys Gln Gly Asp Ser Gly Pro
                500                 505                 510

Leu Thr Cys Glu Lys Asp Gly Thr Tyr Tyr Val Tyr Gly Ile Val Ser
                515                 520                 525

Trp Gly Leu Glu Cys Gly Lys Arg Pro Gly Val Tyr Thr Gln Val Thr
                530                 535                 540

Lys Phe Leu Asn Trp Ile Lys Ala Thr Ile Lys Ser Glu Ser Gly Phe
545                 550                 555                 560
```

<210> SEQ ID NO 6
<211> LENGTH: 560
<212> TYPE: PRT
<213> ORGANISM: Homo sapiens

<400> SEQUENCE: 6

```
Met Phe Ala Arg Met Ser Asp Leu His Val Leu Leu Leu Met Ala Leu
1               5                   10                  15

Val Gly Lys Thr Ala Cys Gly Phe Ser Leu Met Ser Leu Leu Glu Ser
                20                  25                  30
```

-continued

```
Leu Asp Pro Asp Trp Thr Pro Asp Gln Tyr Asp Tyr Ser Tyr Glu Asp
         35                  40                  45

Tyr Asn Gln Glu Glu Asn Thr Ser Ser Thr Leu Thr His Ala Glu Asn
         50                  55                  60

Pro Asp Trp Tyr Tyr Thr Glu Asp Gln Ala Asp Pro Cys Gln Pro Asn
 65                  70                  75                  80

Pro Cys Glu His Gly Gly Asp Cys Leu Val His Gly Ser Thr Phe Thr
                 85                  90                  95

Cys Ser Cys Leu Ala Pro Phe Ser Gly Asn Lys Cys Gln Lys Val Gln
             100                 105                 110

Asn Thr Cys Lys Asp Asn Pro Cys Gly Arg Gly Gln Cys Leu Ile Thr
             115                 120                 125

Gln Ser Pro Pro Tyr Tyr Arg Cys Val Cys Lys His Pro Tyr Thr Gly
     130                 135                 140

Pro Ser Cys Ser Gln Val Val Pro Val Cys Arg Pro Asn Pro Cys Gln
145                 150                 155                 160

Asn Gly Ala Thr Cys Ser Arg His Lys Arg Arg Ser Lys Phe Thr Cys
                 165                 170                 175

Ala Cys Pro Asp Gln Phe Lys Gly Lys Phe Cys Glu Ile Gly Ser Asp
             180                 185                 190

Asp Cys Tyr Val Gly Asp Gly Tyr Ser Tyr Arg Gly Lys Met Asn Arg
             195                 200                 205

Thr Val Asn Gln His Ala Cys Leu Tyr Trp Asn Ser His Leu Leu Leu
    210                 215                 220

Gln Glu Asn Tyr Asn Met Phe Met Glu Asp Ala Glu Thr His Gly Ile
225                 230                 235                 240

Gly Glu His Asn Phe Cys Arg Asn Pro Asp Ala Asp Glu Lys Pro Trp
                 245                 250                 255

Cys Phe Ile Lys Val Thr Asn Asp Lys Val Lys Trp Glu Tyr Cys Asp
             260                 265                 270

Val Ser Ala Cys Ser Ala Gln Asp Val Ala Tyr Pro Glu Glu Ser Pro
    275                 280                 285

Thr Glu Pro Ser Thr Lys Leu Pro Gly Phe Asp Ser Cys Gly Lys Thr
    290                 295                 300

Glu Ile Ala Glu Arg Lys Ile Lys Arg Ile Tyr Gly Gly Phe Lys Ser
305                 310                 315                 320

Thr Ala Gly Lys His Pro Trp Gln Ala Ser Leu Gln Ser Ser Leu Pro
                 325                 330                 335

Leu Thr Ile Ser Met Pro Gln Gly His Phe Cys Gly Gly Ala Leu Ile
             340                 345                 350

His Pro Cys Trp Val Leu Thr Ala Ala His Cys Thr Asp Ile Lys Thr
             355                 360                 365

Arg His Leu Lys Val Val Leu Gly Asp Gln Asp Leu Lys Lys Glu Glu
    370                 375                 380

Phe His Glu Gln Ser Phe Arg Val Glu Lys Ile Phe Lys Tyr Ser His
385                 390                 395                 400

Tyr Asn Glu Arg Asp Glu Ile Pro His Asn Asp Ile Ala Leu Leu Lys
                 405                 410                 415

Leu Lys Pro Val Asp Gly His Cys Ala Leu Glu Ser Lys Tyr Val Lys
             420                 425                 430

Thr Val Cys Leu Pro Asp Gly Ser Phe Pro Ser Gly Ser Glu Cys His
             435                 440                 445

Ile Ser Gly Trp Gly Val Thr Glu Thr Gly Lys Gly Ser Arg Gln Leu
```

```
                450                 455                 460
Leu Asp Ala Lys Val Lys Leu Ile Ala Asn Thr Leu Cys Asn Ser Arg
465                 470                 475                 480

Gln Leu Tyr Asp His Met Ile Asp Asp Ser Met Ile Cys Ala Gly Asn
                485                 490                 495

Leu Gln Lys Pro Gly Gln Asp Thr Cys Gln Gly Asp Ser Gly Gly Pro
            500                 505                 510

Leu Thr Cys Glu Lys Asp Gly Thr Tyr Tyr Val Tyr Gly Ile Val Ser
            515                 520                 525

Trp Gly Leu Glu Cys Glu Lys Arg Pro Gly Val Tyr Thr Gln Val Thr
530                 535                 540

Lys Phe Leu Asn Trp Ile Lys Ala Thr Ile Lys Ser Glu Ser Gly Phe
545                 550                 555                 560

<210> SEQ ID NO 7
<211> LENGTH: 560
<212> TYPE: PRT
<213> ORGANISM: Homo sapiens

<400> SEQUENCE: 7

Met Phe Ala Arg Met Ser Asp Leu His Val Leu Leu Leu Met Ala Leu
  1               5                  10                  15

Val Gly Lys Thr Ala Cys Gly Phe Ser Leu Met Ser Leu Leu Glu Ser
                 20                  25                  30

Leu Asp Pro Asp Trp Thr Pro Asp Gln Tyr Asp Tyr Ser Tyr Glu Asp
             35                  40                  45

Tyr Asn Gln Glu Glu Asn Thr Ser Ser Thr Leu Thr His Ala Glu Asn
 50                  55                  60

Pro Asp Trp Tyr Tyr Thr Glu Asp Gln Ala Asp Pro Cys Gln Pro Asn
 65                  70                  75                  80

Pro Cys Glu His Gly Gly Asp Cys Leu Val His Gly Ser Thr Phe Thr
                 85                  90                  95

Cys Ser Cys Leu Ala Pro Phe Ser Gly Asn Lys Cys Gln Lys Val Gln
            100                 105                 110

Asn Thr Cys Lys Asp Asn Pro Cys Gly Arg Gly Gln Cys Leu Ile Thr
            115                 120                 125

Gln Ser Pro Pro Tyr Tyr Arg Cys Val Cys Lys His Pro Tyr Thr Gly
130                 135                 140

Pro Ser Cys Ser Gln Val Val Pro Val Cys Arg Pro Asn Pro Cys Gln
145                 150                 155                 160

Asn Gly Ala Thr Cys Ser Arg His Lys Arg Arg Ser Lys Phe Thr Cys
            165                 170                 175

Ala Cys Pro Asp Gln Phe Lys Gly Lys Phe Cys Glu Ile Gly Ser Asp
            180                 185                 190

Asp Cys Tyr Val Gly Asp Gly Tyr Ser Tyr Arg Gly Lys Met Asn Arg
            195                 200                 205

Thr Val Asn Gln His Ala Cys Leu Tyr Trp Asn Ser His Leu Leu Leu
210                 215                 220

Gln Glu Asn Tyr Asn Met Phe Met Glu Asp Ala Glu Thr His Gly Ile
225                 230                 235                 240

Gly Glu His Asn Phe Cys Arg Asn Pro Asp Ala Asp Glu Lys Pro Trp
                245                 250                 255

Cys Phe Ile Lys Val Thr Asn Asp Lys Val Lys Trp Glu Tyr Cys Asp
            260                 265                 270
```

```
Val Ser Ala Cys Ser Ala Gln Asp Val Ala Tyr Pro Glu Ser Pro
        275                 280                 285

Thr Glu Pro Ser Thr Lys Leu Pro Gly Phe Asp Ser Cys Gly Lys Thr
290                 295                 300

Glu Ile Ala Glu Arg Lys Ile Lys Arg Ile Tyr Gly Gly Phe Lys Ser
305                 310                 315                 320

Thr Ala Gly Lys His Pro Trp Gln Ala Ser Leu Gln Ser Ser Leu Pro
                325                 330                 335

Leu Thr Ile Ser Met Pro Gln Gly His Phe Cys Gly Gly Ala Leu Ile
                340                 345                 350

His Pro Cys Trp Val Leu Thr Ala Ala His Cys Thr Asp Ile Lys Thr
            355                 360                 365

Arg His Leu Lys Val Val Leu Gly Asp Gln Asp Leu Lys Lys Glu Glu
370                 375                 380

Phe His Glu Gln Ser Phe Arg Val Gln Lys Ile Phe Lys Tyr Ser His
385                 390                 395                 400

Tyr Asn Glu Arg Asp Glu Ile Pro His Asn Asp Ile Ala Leu Leu Lys
                405                 410                 415

Leu Lys Pro Val Asp Gly His Cys Ala Leu Glu Ser Lys Tyr Val Lys
                420                 425                 430

Thr Val Cys Leu Pro Asp Gly Ser Phe Pro Ser Gly Ser Glu Cys His
            435                 440                 445

Ile Ser Gly Trp Gly Val Thr Glu Thr Gly Lys Gly Ser Arg Gln Leu
450                 455                 460

Leu Asp Ala Lys Val Lys Leu Ile Ala Asn Thr Leu Cys Asn Ser Arg
465                 470                 475                 480

Gln Leu Tyr Asp His Met Ile Asp Asp Ser Met Ile Cys Ala Gly Asn
                485                 490                 495

Leu Gln Lys Pro Gly Gln Asp Thr Cys Gln Gly Asp Ser Gly Gly Pro
                500                 505                 510

Leu Thr Cys Glu Lys Asp Gly Thr Tyr Tyr Val Tyr Gly Ile Val Ser
            515                 520                 525

Trp Gly Leu Glu Cys Gly Lys Arg Pro Gly Val Tyr Thr Gln Val Thr
530                 535                 540

Lys Phe Leu Asn Trp Ile Lys Ala Thr Ile Lys Ser Glu Ser Gly Phe
545                 550                 555                 560

<210> SEQ ID NO 8
<211> LENGTH: 560
<212> TYPE: PRT
<213> ORGANISM: Homo sapiens

<400> SEQUENCE: 8

Met Phe Ala Arg Met Ser Asp Leu His Val Leu Leu Leu Met Ala Leu
1               5                   10                  15

Val Gly Lys Thr Ala Cys Gly Phe Ser Leu Met Ser Leu Leu Glu Ser
                20                  25                  30

Leu Asp Pro Asp Trp Thr Pro Asp Gln Tyr Asp Tyr Ser Tyr Glu Asp
            35                  40                  45

Tyr Asn Gln Glu Glu Asn Thr Ser Ser Thr Leu Thr His Ala Glu Asn
        50                  55                  60

Pro Asp Trp Tyr Tyr Thr Glu Asp Gln Ala Asp Pro Cys Gln Pro Asn
65                  70                  75                  80

Pro Cys Glu His Gly Gly Asp Cys Leu Val His Gly Ser Thr Phe Thr
                85                  90                  95
```

-continued

```
Cys Ser Cys Leu Ala Pro Phe Ser Gly Asn Lys Cys Gln Lys Val Gln
            100                 105                 110
Asn Thr Cys Lys Asp Asn Pro Cys Gly Arg Gly Gln Cys Leu Ile Thr
            115                 120                 125
Gln Ser Pro Pro Tyr Tyr Arg Cys Val Cys Lys His Pro Tyr Thr Gly
            130                 135                 140
Pro Ser Cys Ser Gln Val Val Pro Val Cys Arg Pro Asn Pro Cys Gln
145                 150                 155                 160
Asn Gly Ala Thr Cys Ser Arg His Lys Arg Arg Ser Lys Phe Thr Cys
                165                 170                 175
Ala Cys Pro Asp Gln Phe Lys Gly Lys Phe Cys Glu Ile Gly Ser Asp
            180                 185                 190
Asp Cys Tyr Val Gly Asp Gly Tyr Ser Tyr Arg Gly Lys Met Asn Arg
            195                 200                 205
Thr Val Asn Gln His Ala Cys Leu Tyr Trp Asn Ser His Leu Leu Leu
        210                 215                 220
Gln Glu Asn Tyr Asn Met Phe Met Glu Asp Ala Glu Thr His Gly Ile
225                 230                 235                 240
Gly Glu His Asn Phe Cys Arg Asn Pro Asp Ala Asp Glu Lys Pro Trp
                245                 250                 255
Cys Phe Ile Lys Val Thr Asn Asp Lys Val Lys Trp Glu Tyr Cys Asp
            260                 265                 270
Val Ser Ala Cys Ser Ala Gln Asp Val Ala Tyr Pro Glu Glu Ser Pro
        275                 280                 285
Thr Glu Pro Ser Thr Lys Leu Pro Gly Phe Asp Ser Cys Gly Lys Thr
    290                 295                 300
Glu Ile Ala Glu Arg Lys Ile Lys Arg Ile Tyr Gly Gly Phe Lys Ser
305                 310                 315                 320
Thr Ala Gly Lys His Pro Trp Gln Ala Ser Leu Gln Ser Ser Leu Pro
                325                 330                 335
Leu Thr Ile Ser Met Pro Gln Gly His Phe Cys Gly Gly Ala Leu Ile
            340                 345                 350
His Pro Cys Trp Val Leu Thr Ala Ala His Cys Thr Asp Ile Lys Thr
        355                 360                 365
Arg His Leu Lys Val Val Leu Gly Asp Gln Asp Leu Lys Lys Glu Glu
    370                 375                 380
Phe His Glu Gln Ser Phe Arg Val Gln Lys Ile Phe Lys Tyr Ser His
385                 390                 395                 400
Tyr Asn Glu Arg Asp Glu Ile Pro His Asn Asp Ile Ala Leu Leu Lys
                405                 410                 415
Leu Lys Pro Val Asp Gly His Cys Ala Leu Glu Ser Lys Tyr Val Lys
            420                 425                 430
Thr Val Cys Leu Pro Asp Gly Ser Phe Pro Ser Gly Ser Glu Cys His
        435                 440                 445
Ile Ser Gly Trp Gly Val Thr Glu Thr Gly Lys Gly Ser Arg Gln Leu
    450                 455                 460
Leu Asp Ala Lys Val Lys Leu Ile Ala Asn Thr Leu Cys Asn Ser Arg
465                 470                 475                 480
Gln Leu Tyr Asp His Met Ile Asp Asp Ser Met Ile Cys Ala Gly Asn
                485                 490                 495
Leu Gln Lys Pro Gly Gln Asp Thr Cys Gln Gly Asp Ser Gly Gly Pro
            500                 505                 510
```

-continued

```
Leu Thr Cys Glu Lys Asp Gly Thr Tyr Tyr Val Tyr Gly Ile Val Ser
        515                 520                 525

Trp Gly Leu Glu Cys Glu Lys Arg Pro Gly Val Tyr Thr Gln Val Thr
    530                 535                 540

Lys Phe Leu Asn Trp Ile Lys Ala Thr Ile Lys Ser Glu Ser Gly Phe
545                 550                 555                 560
```

MARBURG I MUTANT OF FACTOR VII ACTIVATING PROTEASE (FSAP) AS RISK FACTOR FOR ARTERIAL THROMBOSIS

This application is a continuation-in-part of application Ser. No. 09/912,559 filed Jul. 26, 2001, now U.S. Pat. No. 6,831,167, which claims priority to German Application Nos. 100 36 641.4, filed Jul. 26, 2000, 100 50 040.4, filed Oct. 10, 2000, 100 52 319.6 filed Oct. 21, 2000, and 101 18 706.8, filed Apr. 12, 2001. This application also claims priority to German Application Nos. DE 102 12 246.6, filed Mar. 19, 2002; and DE DE 102 38 429.0, filed Aug. 16, 2002. All of the above-listed applications, in their entirety, are incorporated herein by reference.

The invention relates to mutants of factor VII-activating protease (FSAP) and to reduced blood plasma levels of FSAP as indicators of an increased risk for the development and progression of atherothrombosis (or arterial thrombosis) and of the pathophysiological sequelae resulting therefrom.

Atherosclerosis is a pathological change in the arteries which is associated inter alia with hardening, thickening and loss of elasticity thereof and is regarded as the main cause of myocardial infarction and stroke and of other disorders. Numerous exogenous and endogenous factors are thought to be responsible for the initiation and progression of atherosclerosis, for example hypertension, hyperlipidemia, diabetes, toxins, nicotine, excessive alcohol consumption and inflammations. These influences are referred to as risk factors. However, with the increasing number of studies and improved analytical methods, in recent years further risk factors for atherosclerosis and subsequent arterial thrombosis have been found.

Risk factors are investigated in epidemiological studies, as in the Bruneck study which has become well known among specialists in the field. One thousand inhabitants of Bruneck, Italy, were recruited for this study in 1990. Ultrasound investigations of the carotid artery and analyses of a number of blood parameters and questioning of the subjects made it possible to establish a broad database for further follow-up of the development and progression of atherosclerosis. These investigations were continued on the same subjects and analyzed at 5-year intervals. A model of the development of atherosclerosis and its progression was derived therefrom. As a first result of this study, a connection was found between the development of atherosclerosis and known, traditional risk factors such as the aforementioned hyperlipidemia and other factors. However, if the atherosclerotic plaque reaches such an extent that the blood vessel is occluded by up to 40%, other risk factors become important and may significantly influence the further progress of the atherosclerosis and the vascular occlusion. These factors include in particular plasma proteins which intervene in hemostasis. A reduced coagulation-inhibitory potential contributes to this, e.g. reduced antithrombin or protein C levels, or the so-called APC (activated protein C) resistance. A reduction in the fibrinolytic potential may therefore have a crucial influence on the progression of the vascular occlusion, as is observed for example when the levels of lipoprotein (a) in the blood are raised.

To date, risk factors for venous occlusive disorders have been identified, such as APC resistance (Factor V Leiden). The extent to which a given risk factor increases the risk for a condition may be expressed as an "odds ratio." The odds ratio for venous occlusive disorders in heterozygotes for the APC resistance mutation has been reported to be about 5 to 8, compared with subjects without APC resistance. For arterial occlusive disorders, on the other hand, this risk factor has been reported with low odds ratios of average about 2.

The plasma samples and DNAs available from the subjects in the Bruneck study were therefore investigated once again for the presence of other risk factors for atherosclerosis, directing particular attention at recently found mutants of coagulation factor VII-activating protease (=FSAP), referred to hereinafter as the FSAP Marburg I and Marburg II mutations.

German patent application 199 03 693.4 discloses a protease which can be isolated from blood plasma and which is able to activate coagulation factor VII. This protease is also referred to as factor seven-activating protease (FSAP) (or as PHBP or PHBSP, corresponding to plasma hyaluronic acid-binding (serine) protease). FSAP therefore has procoagulant properties. A particular property of FSAP is that of activating single-chain plasminogen activators, such as prourokinase or single-chain tissue plasminogen activator (sct-PA). However, alone or in combination with plasminogen activators, FSAP can also be used correspondingly to assist fibrinolysis, for example, in cases of thrombotic complications.

The test systems which are now available and are described in the German patent applications 199 03 693.4 and 199 26 531.3 make it possible not only to detect FSAP but also to quantify the FSAP antigen content and determine the activity thereof in plasma. The antigen determination is preferably carried out by means of an ELISA test. On the other hand, the activity can in principle be determined through activation of prourokinase to urokinase and conversion of a chromogenic substrate with subsequent extinction difference measurement.

German patent application 100 52 319.6 discloses the use of these test systems in investigations on healthy blood donors in which 5 to 10% of subjects were identified as having an average FSAP antigen content but a markedly reduced potential for activation of prourokinase. Since this probably also applied to the isolated, individual proteases, the corresponding DNAs were analyzed for further investigation from blood cells. It was surprisingly possible in this case to identify in particular a mutation (single nucleotide polymorphism; SNP; G/A in position 1601). This modification leads in the protein to a Gly to Glu amino acid exchange in position 511 of the mature protein or in amino acid position 534 of the FSAP proenzyme including the signal peptide. This amino acid exchange results in FSAP losing the ability to activate prourokinase to urokinase or at least suffering a considerable diminution in activity. The aforementioned mutation, called FSAP Marburg I, has to date been found in all samples having an average antigen content but a reduced activity in the formation of urokinase from prourokinase. These results are described, for example, in U.S. application Ser. No. 09/912,559, to which this application claims priority, and which is incorporated herein by reference.

For example, genomic DNA from the blood of two subjects with reduced activity and from four subjects with normal prourokinase activity was isolated, all exons amplified and then the FSAP DNA sequence was determined using the PCR primers. The result is shown in Table 1. A total of 4 nucleotide positions in the coding region were polymorphic, i.e. at these positions two bases were detected simultaneously. It can therefore be assumed that these cases are heterozygous, having one wild type and one mutant allele. Two of these (at positions 183 and 957) are third base exchanges that do not result in amino acid exchange. The other two, which were found only in the DNA of the subjects with reduced prourokinase activity, lead to amino acid exchanges as depicted in Table 1.

TABLE 1

DNA sequence at nucleotide positions*

| Subject No. | ProUK activity | 183 | 957 | 1177 | 1601 |
|---|---|---|---|---|---|
| S83182 |  | T | G | G | G |
| 9689 | normal | T/C | G | G | G |
| 9690 | normal | T/C | G | G | G |
| 9704 | normal | T | G | G | G |
| 9706 | normal | T | G | G | G |
| 9714 | reduced | T | G | G/C | G/A |
| 9715 | reduced | T | G | G/C | G/A |

*where 1 is A of the start codon.

Amino acid at position*

| Subject No. | ProUK activity | NT*:183 AA*:61 | NT:957 AA:319 | NT:1177 AA:393 | NT:1601 AA:534 |
|---|---|---|---|---|---|
| S83182 |  | His | Lys | Glu | Gly |
| 9689 | normal | His | Lys | Glu | Gly |
| 9690 | normal | His | Lys | Glu | Gly |
| 9704 | normal | His | Lys | Glu | Gly |
| 9706 | normal | His | Lys | Glu | Gly |
| 9714 | reduced | His | Lys | Glu/Gln | Gly/Glu |
| 9715 | reduced | His | Lys | Glu/Gln | Gly/Glu |

*NT-Nucleotide position;
AA-amino acid position, where 1 is the methionine of the leader peptide.

In order to study the correlation of the two FSAP mutations with Reduced prourokinase activating potency, the DNA of further individuals was Sequenced at these positions. The result is summarized in Table 2. All 6 subjects Having reduced prourokinase activating potency were heterozygous at the nucleotide Position 1601 (Gly-Glu exchange at amino acid 534), and four were additionally heterozygous at nucleotide position 1177 (Glu-Gln exchange at amino acid 393). None of the 11 subjects in total having normal prourokinase activating potency or prourokinase activating potency in the lower normal range had the abovementioned heterozygosities. This result suggests that the exchange in amino acid position 534 is causally linked to reduced prourokinase activity.

TABLE 2

| Subject | | | DNA sequence at nucleotide position | |
|---|---|---|---|---|
| No. | FSAP antigen | ProUK activity | 1177 | 1601 |
| 9714 | Normal | Low | C/G | A/G |
| 9715 | Normal | Low | C/G | A/G |
| 9802 | Normal | Low | C/G | A/G |
| 10032 | Normal | Low | G | A/G |
| 10039 | Normal | Low | C/G | A/G |
| 10047 | Normal | Low | G | A/G |
| 9698 | Lower normal range | Lower normal range | G | G |
| 9702 | Lower normal range | Lower normal range | G | G |
| 9711 | Lower normal range | Lower normal range | G | G |
| 9712 | Lower normal range | Lower normal range | G | G |
| 10038 | Lower normal range | Lower normal range | G | G |
| 9689 | Normal | Normal | G | G |
| 9690 | Normal | Normal | G | G |
| 9704 | Normal | Normal | G | G |
| 9706 | Normal | Normal | G | G |
| 9803 | Normal | Normal | G | G |
| 10043 | Normal | Normal | G | G |

Some embodiments of this invention therefore relate to an atherothrombosis risk factor that consists of a mutant of coagulation factor VII-activating protease (FSAP). In some embodiments of this invention, the risk factor is a mutant in which the FSAP proenzyme, including the signal peptide, has a Gly/Glu exchange at amino acid position 534. This mutation is herein called the Marburg I mutation.

The corresponding nucleotide sequence of the FSAP proenzyme including the signal peptide shows a G/A base exchange at nucleotide position 1601. The sequences of the above FSAP species are provided in Table 3.

The Marburg I mutation is sometimes found together with a Glu/Gln exchange at position 393 (position 370 in the mature FSAP protein without the leader sequence), resulting from a G to C mutation at position 1177 in the nucleotide sequence corresponding to the FSAP proenzyme including the signal peptide. The Glu/Gln exchange at position 393 is herein called the Marburg II mutation.

TABLE 3

| SEQ ID NO. | Description | NT:1177 AA:393 | NT:1601 AA:534 |
|---|---|---|---|
| 1 | wild-type nucleotide | G | G |
| 2 | Marburg I nucleotide | G | A |
| 3 | Marburg II nucleotide | C | G |
| 4 | Marburg I and II nucleotide | C | A |
| 5 | wild-type protein | Glu | Gly |
| 6 | Marburg I protein | Glu | Glu |
| 7 | Marburg II protein | Gln | Gly |
| 8 | Marburg I and II protein | Gln | Glu |

A PCR test for the Marburg I and II mutations was established and used to investigate the DNA of the subjects recruited for the Bruneck study. The FSAP Marburg I mutation was found in 4.5% of all the samples analyzed. These findings were then assessed using the individual data collected during the study to assess the development and progression of atherosclerosis.

Surprisingly, the Marburg I mutation correlates with an increased risk of developing arterial atherosclerosis. An odds ratio of about "6.6" was calculated for this FSAP mutation, i.e. a risk on the arterial side that is comparable with the risk of APC resistance in the venous region. In this study the Marburg I polymorphism was the risk factor with the highest odds ratio of all factors investigated, as shown in table 4. It is particularly surprising that this mutation represents an independent risk factor, making its own, marked contribution to the development and progression of atherosclerosis after allowance for all previously known risk factors. This realization and the determination of the sequences corresponding to the FSAP Marburg I mutation may therefore improve the prospects of diagnosing and treating heart diseases and vascular disorders caused by atherosclerosis.

Atherothrombosis frequently leads, for example, to coronary artery disease followed by myocardial infarctions. Depending on the vessels affected, the organ supplied thereby becomes involved. In the case of the carotid artery, this results in the brain being undersupplied with nutrients and oxygen and may, in the worst case, lead to a stroke. Other organs affected by atherothrombosis and subject to the risk of vascular occlusive disease and the sequelae resulting therefrom are also affected by the FSAP Marburg I mutant. This may result, for example, in disorders of the kidneys, liver, lungs, and other disorders.

Thus, the risk factor of this invention may indicate a genetic predisposition to arterial thrombosis, and/or a genetic predisposition to the development of thromboses. The risk factor may also indicate a genetic predisposition to the development of atherosclerotic disorders and their sequelae, such as coronary artery disease, acute myocardial infarction, pulmonary embolism, peripheral artery occlusion, acute ischemic stroke, and thromboembolism, in addition to arterial thrombosis. The risk factor may also indicate a genetic predisposition to thrombotic disorders and their sequelae, such as arterial and venous thrombosis, deep vein thrombosis, acute myocardial infarction, pulmonary embolism, peripheral artery occlusion, acute ischemic stroke, and thromboembolism. The risk factor may also indicate a genetic predisposition to at least one of arterial and venous occlusive disorders, to at least one of atherosclerotic and thrombotic restrictions of organ functions, as well as to one or more of angina pectoris, myocardial infarction, and strokes.

Methods for examining the structure, sequence, and activity of the FSAP Marburg I and II mutants are described in the aforementioned German patent applications, in particular in German patent application 1090 52 319.6, as well as in U.S. application Ser. No. 09/912,559, all of which are incorporated herein by reference. These methods include measurement of the FSAP protease activity, preferably in combination with an FSAP antigen test, and determination of the nucleotide sequence in the mutated region by suitable test systems.

The arterial thrombosis risk factor of the invention may thus be defined as one or more FSAP mutants that have lost the ability to activate single-chain plasminogen activators or for which this ability is at least impaired. In some embodiments, the risk factor is characterized by an FSAP mutant that has lost the ability to activate prourokinase or for which this ability is reduced.

A genetic predisposition to the development of arterial thrombosis can thus be identified by detecting one or more of the aforementioned FSAP mutants. Detection, as used herein, means determining if a mutant FSAP is present in a sample. Detection may be carried out by a variety of methods, as described below.

Detection of these FSAP mutants also indicates the predisposition to the development of arterial thromboses and the predisposition to the development of atherosclerotic or thrombotic disorders and their sequelae, such as arterial and venous occlusive disorders, coronary artery disease, acute myocardial infarction, pulmonary embolism, peripheral artery occlusion, acute ischemic stroke, deep vein thrombosis, and thromboembolism. The predisposition to development of atherosclerotic or thrombotic restrictions of organ functions is a frequent cause of angina pectoris, myocardial infarction or strokes. It is typical of all cases that the potential for activation of single-chain plasminogen activators, such as single-chain tissue plasminogen activator (sc-tPA), and single-chain urinary plasminogen activator (sc-uPA), or prourokinase, is reduced. The reduction of this activation potential can be detected in the blood but especially in the plasma.

In view of the great importance of FSAP mutants as atherothrombosis or arterial thrombosis risk factors, diagnostic methods for detecting them are very important. They may be based on determining at least one of a reduced FSAP antigen concentration and a reduced activity of FSAP in the body fluids of an individual. This may entail determination of the potential for activation of single-chain plasminogen activators, such as prourokinase, in the body fluids.

In the context of the present invention, an individual, or donor, may be a mammal, such as a human. Relevant body fluids include whole blood, blood plasma, serum, as well as lymphatic, cerebrospinal, pleural, pericardial, peritoneal, and synovial fluids, tears, seminal plasma, and cell lysates.

Some embodiments of the invention include detecting heterozygous or homozygous mutants of the FSAP proenzyme gene with a G/A base exchange at nucleotide position 1601 by analysing the genomic DNA of an individual, or the mRNA or cDNA derived therefrom. Some embodiments of the invention include detecting heterozygous or homozygous mutants of the FSAP proenzyme gene with a G/C base exchange at position 1177. In some embodiments, both of these base exchanges may be detected.

In other embodiments, FSAP mutants may be detected at the protein level. Specific monoclonal or polyclonal antibodies may be used for this purpose, as well as their corresponding Fab or F(ab')$_2$ fragments. Histological investigation methods on tissues or in solutions extracted from tissues are also available. For examples of relevant tissues in the context of this invention, see table 4 below.

Exemplary antibodies are those specific for one or more of wild-type FSAP, including its proenzyme with or without the signal sequence, and its fragments; and FSAP mutants comprising at least one of a Glu to Gln exchange at amino acid position 393 and a Gly to Glu exchange at amino acid position 534, as well as their proenzymes with or without the signal sequence, and their fragments. Antibodies herein that specifically recognize both wild-type and mutant FSAP sequences, such as sequences corresponding to full-length active enzymes, proenzymes and enzyme fragments, are termed "FSAP-specific," while those that are specific for only wild-type or only mutant FSAP sequences are termed "wild-type FSAP-specific" and "mutant FSAP-specific," respectively.

In some embodiments, the diagnostic method includes incubating a sample that might contain FSAP mutant(s) with a first antibody immobilized on a solid support, and, after washing, adding a second, labelled antibody, washing again and measuring the signal elicited by the second antibody, wherein the second, labelled antibody may be a wild-type FSAP-specific antibody.

Another method comprises incubating a sample that might contain FSAP mutant(s) with a first, wild-type FSAP-specific antibody, immobilized on a solid support, and, after washing, adding a second, labelled antibody, washing again and measuring the signal elicited by the second antibody.

A further method comprises immobilizing the sample that might contain FSAP mutant(s) on a support, adding a labelled antibody, alone or mixed with an unlabelled antibody, and detecting the labelled antibody.

Yet another method comprises mixing an antibody immobilized on a support with the sample that might contain FSAP mutant(s) in the presence of a labelled FSAP mutant, and measuring the signal elicited by the label.

In the methods described above, the first or second antibodies, unless stated otherwise, may include FSAP-specific, wild-type FSAP-specific, or mutant FSAP-specific antibodies.

An example diagnostic method in which the activity of FSAP is measured comprises incubating an FSAP-containing sample on a solid support onto which an FSAP-specific antibody has previously been coupled, and then, after washing out the free support, incubating the FSAP immobilized thereon with reagents that allow determination of FSAP activity.

Some embodiments include diagnostic methods in which antibodies are used to detect FSAP mutants by Western blotting for immunohistology, fluorescence-activated cell sorting (FACS), or comparable methods.

The diagnostic methods of the invention may also be carried out by the ELISA technique. This entails binding an FSAP and/or FSAP mutant to a matrix, for example to a microtiter plate. For optimal presentation of the FSAP and/or FSAP mutant, it is possible to coat the plate with monoclonal or polyclonal antibodies, or the $F(ab')_2$ or Fab fragments thereof, before loading with FSAP and/or FSAP mutants. Since FSAP and FSAP mutants generally bind very well to dextran sulfate, heparin and similar substances, coating with these agents is also possible prior to loading with FSAP and/or FSAP mutants. After the support or microtiter plate has been washed, it is blocked where appropriate with the agents known for this purpose, such as detergent or albumin, washed and then incubated with the solution to be tested. The solutions containing FSAP-specific antibodies include blood serum, plasma, and other body fluids, as well as synovial fluids, cerebrospinal fluid, saliva, tears, seminal plasma or cell lysates.

Incubation and washing of the support is followed by use of a suitable detection reagent. The test substances required for detecting the various antibody classes, such as IgG, IgM, IgA, IgE, and the relevant subclasses, are commercially available as labelled reagents. Detection and quantification of the antibody titer can then take place by a photometric examination, for example, by measurement of the extinction brought about by cleavage of a chromogenic substrate by an enzyme coupled to the anti-human antibody. It is also possible to measure the fluorescence emitted by a fluorescent group connected to the antibody used for the detection. In addition, it is possible to carry out the detection with a radiometric measurement, if the substance used for detection is labelled with a radioactive group. Diagnostic methods in which the bound human antibodies are incubated with a labelled anti-human immunoglobulin or fragments thereof, or labelled protein A or protein G, and in which the signal emitted by the bound, labelled substance is determined, have already proved very suitable in many instances.

It is also possible to detect the antibodies by a photometric measurement of the extinction caused by cleavage of a suitable chromogenic or fluorogenic substrate by enzyme-coupled anti-human antibodies or fragments thereof, or protein A or protein G. Diagnostic methods in which antibodies are detected by measuring the fluorescence caused by a bound substance labelled with fluorescent groups are also suitable.

In some embodiments, monoclonal antibodies were prepared and characterized as follows:

Immunization

Three female balb/c mice (approx. 6 weeks old) were immunized with FSAP. The first injection consisted of 0.2 ml of the antigen (10 µg) mixed with 0.2 ml of complete Freund's adjuvant. In the three following boost injections (each 2 weeks apart) the antigen (20 µg in 0.2 ml) was administered without adjuvant (all injections i.p.). The immunogen was diluted in PBS. After the last injection, the serum titer was determined by means of indirect ELISA by coating a microtiter plate with FSAP. The mouse with the highest serum titer was selected for the fusion.

Fusion

About three weeks after the last application, the antigen was administered on three successive days (10 µg in 0.1 ml i.v.). On the next day (day 4) the mouse was sacrificed after taking blood. The spleen was removed and the spleen cells were isolated. The spleen cells were then fused with the murine myeloma cell line SP2/0-Ag 14. The fusion reagent was polyethylene glycol 4000 (Merck). The fusion was carried out using a modification of the original Köhler/Milstein method. The cells were distributed on 24-well culture plates. The medium used was Dulbecco mod. Eagle's medium with 10% fetal calf serum and HAT for selection. After about two weeks, the cell clones grown were transferred to the wells of a 48 well plate and coded.

Hybridoma Screening

The culture supernatant was taken from 1728 grown clones and assayed by means of ELISA for the presence of mouse IgG. With the aid of immobilized FSAP, mouse IgG-positive supernatants were tested for specificity (ELISA). Of the cell lines assayed, 108 cell lines were identified as specific for FVII activator and stored in the frozen state.

The two hybridoma cell lines denoted DSM ACC2453 and DSM ACC2454 were selected for further studies. These cell lines were deposited on Apr. 5, 2000, with the DSMZ—Deutsche Sammlung Von Mikroorganismen und Zellkulturen GmbH, a depository which is subject to the Treaty of Budapest regulations. The specificity of the antibodies produced by said cell lines was confirmed by BIACORE and binding kinetics were determined. The two monoclonal antibodies are of the IgG1 type.

With the aid of the described antibodies against FSAP wild type and against its mutants, it is possible to carry out diagnostic methods for detecting the mutants by:

a) incubating a sample that could contain one or more FSAP mutants with a first antibody, immobilized on a solid support, then, after washing, adding a second, labeled antibody and, after washing out again, measuring the signal produced by the second antibody, wherein the second antibody may comprise a wild-type FSAP-specific antibody; or b) incubating a sample that could contain one or more FSAP mutants with a first antibody immobilized on a solid support, then, after washing, adding a second, labeled antibody and, after washing out again, measuring the signal produced by the second antibody, wherein the first antibody is a wild-type FSAP-specific antibody; or c) immobilizing a sample that could contain one or more FSAP mutants on a support and detecting the sample with a labeled antibody, alone or in a mixture with an unlabelled antibody; or d) incubating a sample that could contain one or more FSAP mutants with an antibody immobilized on a support in the presence of a labeled FSAP mutant, and measuring the signal produced by the label.

Antibody fragments, such as Fab and $F(ab')_2$ fragments, may also be used in the diagnostic methods in some embodiments.

An example diagnostic method in which the FSAP activity is measured may include incubating the protease-containing sample with a solid support to which at least one of an FSAP-specific antibody, a wild-type FSAP-specific antibody, or a mutant FSAP-specific antibody has been coupled beforehand and, after washing out the solid support, incubating the FSAP fixed to the support with reagents which allow determination of its activity.

In this connection, FSAP activity, such as protease activity, can be measured by photometric determination of the extinction appearing following the action on chromogenic substrates.

It is also possible to determine FSAP protease activity by measuring:
 its action of inactivating blood clotting factors VIII/VIIIa or V/Va or
 its action of shortening blood clotting times in global clotting assays or
 its action of activating plasminogen activators or
 its action of activating blood clotting factor VII.

In some embodiments, FSAP action of activating plasminogen activators may be measured, by examining FSAP activation of the
 single-chain urokinase (scuPA, single chain urokinase plasminogen activator) or the
 single-chain-tPA (sctPA, single chain tissue plasminogen activator).

The mutations responsible for the reduction of prourokinase activating potency can be detected at the DNA and RNA level by using methods that are also used for detecting single nucleotide polymorphisms, for example
 cDNA amplification of mRNA or amplification of the genomic DNA and sequencing;
 detection of the mutation at the cDNA level or genomic DNA level or their amplification by
 hybridization with sequence-specific probes which may also carry labels for the detection, such as enzymes, alkaline phosphatase, HRP and their substrates, fluorescent dyes, also reporter-quencher pairs (such as, for example, scorpions, molecular beacons, TaqMan probes), radioisotopes, chromophores, chemiluminescence labels and electrochemiluminescence labels) or
 methods such as selective 2'-amine acylation, electrochemical oxidation of nucleic acids by "minor groove binder" oligonucleotide conjugates, or by HPLC.

On the basis of the test results which were obtained by the abovementioned antigen assays and activity assays it was possible to study three groups of healthy donors regarding potential mutations at the genomic level. For this purpose, blood was taken from the donors and the blood cells were separated from the plasma by centrifugation. The plasmas were then used to quantify the FSAP antigen and activity levels and were divided according to the latter into three groups, namely into "normal/normal," "lower normal range/lower normal range" and "normal/low." The blood cells obtained were then used to extract genomic DNA and determine the FSAP genotype. The results depicted above in Table 2 were determined.

Based on these results, it is now possible to detect rapidly one or both of the mutants described, whether their genotype is heterozygous or homozygous, at the level of the corresponding FSAP nucleotide sequence. Whereas the abovementioned antigen and activity assays reflected quite well the genotype in a healthy donor, this can become difficult or impossible when the FSAP plasma levels are influenced. Thus, parameters such as hormonal fluctuations, lifestyle, etc., as well as pathological conditions, may strongly influence antigen and/or activity levels. As described in the German Patent application 199 26 531.3, the measurable FSAP activity during a heart attack can increase markedly compared with the normal value with scarcely increased antigen content. As a result, donors that have a reduced FSAP activity when healthy, now appear to be "average."

For example, studies on whether patients with FSAP mutations run an increased risk of suffering thrombotic complications such as heart attacks are possible only with difficulty, owing to the abovementioned restrictions. On the other hand, for example, liver failures may lead to reduced plasma levels, and this likewise may lead to misinterpretations of the "true" genetic predisposition. In contrast, a FSAP mutation assay at the DNA and/or RNA level is independent of temporary events. The combination of all of the assays mentioned allows a complete picture of the donor/patient, i.e. the evaluation of a potential mutation and of the acute state regarding an influence on the antigen-activity ratio. This may result in prophylactic and therapeutic measures.

As described above, heterozygous individuals whose blood plasma contains normal FSAP at about 50% and the FSAP mutant at about 50% have been found. This results in an about 50% reduced activity level of plasmas in which both types of FSAP molecules are present. A very small proportion of individuals was found to be homozygous, their blood plasma containing the FSAP mutant at 100%, in which the prourokinase activation potency was virtually abolished. Plasma pools which have been obtained from the blood of 100 and more donors therefore also contain 5 to 10% of FSAP mutants, depending on the population. This results in a corresponding probability to receive, in blood transfusions, donor blood plasma that contains an FSAP mutant. If blood containing an FSAP mutant is administered to a recipient who cannot produce the mutant, the mutant may be recognized as extraneous and appropriate antibodies can be generated. Subsequent administration of the FSAP mutant at a later stage may lead to immunological reactions in the recipient, the side effects of which are familiar to the skilled worker.

Conversely, in a homozygous blood recipient who produces only an FSAP mutant but not normal FSAP, the latter is recognized as "extraneous" and the appropriate antibodies against it are produced.

FSAP affects hemostasis and the cellular processes connected therewith. By involvement in blood clotting and/or fibrinolysis, it also affects the wound healing reaction. Moreover, FSAP, due to its property of having a high affinity to glycosaminoglycans, can bind to cells and other matrices and therefore is probably physiologically and pathophysiologically involved in cell migration and cellular-proteolytic processes.

FSAP-specific antibodies thus may influence all FSAP-mediated activities. In the case of autoantibodies against FSAP appearing, it is possible that, in addition to an impairment of the physiological functions, immunocomplexes (FSAP+antibody) contribute to side effects of known autoimmune diseases. This may lead, for example, to vasculitides locally in the endothelium. Neutralization of FSAP activity as a profibrinolytic agent could also contribute to a thrombosis-promoting state.

There is, therefore, a need for a diagnostic method for detecting the above described antibodies.

Some embodiments of the invention, therefore, relate to diagnostic methods for detecting antibodies against factor VII-activating protease (FSAP) and/or against one or more FSAP mutants formed by the exchange of one or more amino acids. The method may comprise mixing a sample which could contain antibodies reactive with the FSAP and/or FSAP mutants fixed to a solid support, incubating, and, after washing, detecting the antibody bound to the FSAP(s) with a labeled human anti-immunoglobulin or a labeled protein A and determining the signal emitted by the bound labeled substance.

This diagnostic method may also be carried out using the ELISA technique in which FSAP and/or one or more FSAP mutants are bound to a matrix, for example, to a microtiter plate. For optimal presentation of the FSAP and/or FSAP mutants, the plate may be coated beforehand with monoclonal or polyclonal antibodies or their $F(ab')_2$ or Fab fragments prior to loading the plate with the FSAP and/or FSAP mutants. Since FSAP and its mutants generally bind very well to dextran sulfate, heparin and similar substances, prior coating with these agents before FSAP binding is also possible. After washing, the support or the microtiter plate may additionally be blocked and washed using agents known for this purpose, such as detergent or albumin, and then incubated with the solution to be assayed. FSAP antibody-containing solutions may include blood serum, plasma and other body fluids, such as synovial fluids, CSF, sputum, tears, and seminal plasma, as well as cell lysates.

After incubating and washing the support, a suitable detection agent is then used. The assay substances necessary for detecting the various antibody classes such as IgG, IgM, IgA, IgE and the subclasses belonging thereto, are commercially available as labeled reagents. The antibody titer may be detected and quantified by a photometric determination measuring the extinction caused by cleavage of a chromogenic substrate by an enzyme coupled to the anti-human antibody. It is also possible to measure fluorescence emitted by a fluorescent group linked to an antibody used for detection. It is also possible to carry out the detection using radiometric measurement, if the substance used for detection is labeled with a radioactive group.

The determination of antibodies against FSAP and/or in particular FSAP mutants makes it possible to identify the risk involved in a blood transfusion prior to carrying out the transfusion and to avoid dangerous complications by suitable measures.

Some embodiments of the invention relate to a diagnostic method for immunohistochemical detection of the blood clotting factor VII-activating protease (FSAP), its proenzyme, its mutants, or its fragments. The method may comprise letting an FSAP-specific, labeled, monoclonal or polyclonal antibody, or one of its fragments, react with a tissue sample, washing out the unbound antibody or its fragments, and determining the signal emitted from the bound antibody or one of its fragments.

The method may also be carried out by letting an unlabelled monoclonal or polyclonal antibody or antibody fragment, directed against FSAP, its proenzyme, its mutants, or its fragments, react with a tissue sample, washing out the unbound antibody or its fragments, then letting a labeled anti-antibody or its fragments react with the tissue sample, and, after washing out the unbound labeled anti-antibody, determining the signal emitted from the bound anti-antibody or its fragments.

It was also found that monoclonal or polyclonal antibodies directed against FSAP are very well suited to detecting FSAP in tissue sections of human origin, when the antibodies are labeled with chromophoric or luminescent groups. FSAP-specific polyclonal antibodies obtained by immunization of rabbits, sheep, goats, or other mammals are suitable for the detection as well as monoclonal antibodies. Particularly suitable for the histological specific detection of FSAP which may be present both in the active form and in the proenzyme form, as well as in a fragment, are the monoclonal antibodies of hybridoma cell lines DSM ACC 2453 and DSM ACC 2454. Complexes of activated FSAP with inhibitors such as antiplasmin may also be detected in this way. Suitable for this purpose are all common histological detection methods such as light microscopy, fluorescence microscopy and electron microscopy.

Suitable for detecting FSAP in the abovementioned methods are both the complete polyclonal and monoclonal antibodies and their fragments such as $F(ab')_2$ or Fab, as long as they are labeled with a detectable group. The abovementioned antibodies or their fragments may be applied alone or as a mixture. This is particularly recommended in case one of the recognized epitopes is obscured. For example, a protein domain may not be accessible for an antibody due to cellular association, but is bound by another antibody having specificity for a different FSAP region. Antibodies which are directed against human FSAP, such as against one or more of the wild type and mutants of human FSAP, and which are described in more detail in the German Patent application 100 52 319.6 may also be employed for detection of FSAP in tissue sections of human origin.

The findings obtained so far on the immunohistochemical detection of FSAP can be summarized as follows:

FSAP is detected in almost all of the human tissues studied up until now;

endocrinologically active cells such as Leydig cells or the endocrinologically active cells of the islets of Langerhans of the pancreas are very strongly stained intracytoplasmatically using antibodies against FSAP carrying chromophoric groups;

epithelia and endothelia display according to their location a more or less strong intracytoplasmatic immunoreaction with antibodies against FSAP;

gangliocytes and dendrites of the cortex display high concentrations of FSAP, and this is detected by a strong immunohistological color reaction with chromophoric antibodies;

plasma cells display an intensive intracytoplasmatic coloration with chromophoric antibodies against FSAP;

mesenchymal stroma cells display in complex tissues only a weak or no color reaction toward FSAP.

FSAP is thus a protein that can be regarded as a normal cell constituent. So far FSAP was found located both intracellularly and extracellularly, with the former compartment being markedly more stainable. The inventive detection of FSAP by the mentioned antibodies or their fragments makes it possible to identify the following pathological processes:

endocrinologically active tumors and neuro-endocrine tumors;

angiogenic endothelia and endothelia of the capillary endothelium; and also angiogenically active tumors such as gliomas and glioblastomas, but also, for example, vascular tumors such as hemangioendothelioma or hemangiopericytoma and angiosarcoma;

wound healing reactions, granulation tissue and collagenoses;

atherosclerotic, (micro)thrombosed and necrotic areas;

neurodegenerative disorders such as Alzheimer's disease, Parkinson's disease or as spongiform encephalitides, for example caused by prion proteins;

gammopathies and myelomas.

FSAP may be detected by using monoclonal antibodies of hybridoma cell lines DSM ACC 2453 or DSM ACC 2454.

The diagnostic method of the invention is illustrated in more detail by the following example.

EXAMPLE I

The immunohistochemical reactivity of the FSAP-specific monoclonal antibodies of hybridoma cell lines DSM ACC 2453 and DSM ACC 2454 was studied by preparing from adult human tissue and malignant urological tumors 10 μm thick paraffin sections and subsequently de-waxing the sections which were treated in citrate buffer in the microwave for 3 times 5 minutes. First, an unlabelled antibody of the abovementioned hybridoma cell lines was allowed to react with the sections for 30 minutes. After washing out the tissue section, a labeled anti-mouse detection antibody was allowed to react with the tissue likewise for 30 minutes and then the bound FSAP antibody was made visible by forming the APAAP complex (Alkaline Phosphatase/Anti-Alkaline Phosphatase complex) and by staining with chromogen and counterstaining with hemalum.

As a negative control, each tissue was separately incubated with the detection antibody—without prior incubation with the FSAP antibody—in order to make potential unspecific reactions of the detection visible. In addition an antibody against α-keratin was included as a positive control.

The results of the immunohistochemical study of normal human tissue are summarized in Table 4.

TABLE 4

Antibodies against FSAP, clone DSMZ ACC2454 and DSMZ ACC 2453
Human normal tissue

|  | 2454 | 2453 |  | 2454 | 2453 |
|---|---|---|---|---|---|
| Esophagus |  |  | Appendix |  |  |
| Squamous epithelium | 2+ | 2+ | Epithelia | 1+ | 3+ |
| Secretory units | 0 | 0 | Musculature | 1+ | 1+ |
| Acinar ducts | 2+ | 2+ | Lymphatic follicle | 1+ | 2+ |
| Musculature | 1+ | 1+ | Plasma cells | 2+ | 3+ |
| Stroma | 1+ | 1+ – 2+ | Vascular endothelium | 1+ | 1+ |
| Vascular endothelium | 2+ | 2+ | Pancreas |  |  |
| Cardia (stomach) |  |  | Epithelia | 1+ | 2+ |
| Foveolar epithelium | 0 | 0 | Islets of Langerhans | 3+ | 1+ |
| Glandulae cardiacae | 1+ | 2+ | Duct epithelium | 2+ | 2+ |
| Mucous secretory units | 0 | 0 | Vascular endothelium | 1+ | 1+ |
| Oxyntic glands | 3+ | 3+ | Salivary gland |  |  |
| Musculature | 1+ | 1+ | Mucous end units | 0 | 0 |
| Vascular endothelium | 1+ | 1+ | Serous end units | 1+ | 1+ – 2+ |
| Corpus (stomach) |  |  | Acinar ducts | 1+ | 1+ |
| Foveolar epithelium | 0 | 0 – 1+ | Striate ducts | 1+ | 1+ |
| Corpus gland body | 2+ | 2+ | Vascular endothelium | 0 – 1+ | 0 – 1+ |
| Musculature | 0 | 1+ | Liver |  |  |
| Vascuiar endothelium | 1+ | 1+ | Hepatocytes | 2+ | 2+ |
| Duodenum |  |  | Bile ducts | 0 | 0 |
| Epithelia | 0 – 1+ | 1+ | Vascular endothelium | 1+ | (1+) |
| Brunner's glands | 0 | 0 | Gall bladder |  |  |
| Musculature | 0 | 0 – 1+ | Epithelia | 1+ | 1+ |
| Lymphatic follicle | 1+ | 2+ | Musculature | 2+ | 1+ |
| Ganglion cells | 2+ | 3+ | Vascular endothelium | 2+ | 1+ |
| Vascular endothelium | 1+ | 1+ | Cystic duct |  |  |
| Small intestine |  |  | Epithelium | 3+ | 3+ |
| Epithelia | 2+ | 3+ | Musculature | 2+ | 1+ |
| Musculature | 1+ | 1+ | Ganglion cells | 3+ | 3+ |
| Stroma | 1+ | 2+ | Vascular endothelium | 2+ | 2+ |
| Ganglion cells | 3+ | 3+ | Testis |  |  |
| Vascular endothelium | 1+ | 1+ | Leydig cells | 3+ | 1+ |
| Colon/Rectum |  |  | Sertoli cells | 1+ – 2+ | 1+ |
| Epithelia | 1+ | 1+ | Germ cells | 1+ – 2+ | 1+ |
| Lymphatic follicles | 1+ | 1+ | Vascular endothelium | 1+ | 1+ |
| Plasma cells | 1+ | 1+ | Rete testis |  |  |
| Vascular endothelium | 1+ | 0 | Epithelium | 2+ | 2+ |
| Epididymis |  |  | Placenta |  |  |
| Epididymis duct | 2+ | 2+ | Chorionic epithelium | 3+ | 2+ |
| Efferent ductulus | 2+ | 2+ | Amniotic epithelium | 2+ | 2+ |
| Stroma | 1+ | 1+ | Decidual cells | 2+– 3+ | 2+ |
| Vascular endothelium | 1+ | 1+ | Stroma cells | 0 | +/– |

TABLE 4-continued

Antibodies against FSAP, clone DSMZ ACC2454 and DSMZ ACC 2453
Human normal tissue

| | 2454 | 2453 | | 2454 | 2453 |
|---|---|---|---|---|---|
| Seminal gland | | | Vascular endothelium | 1+ | 1+ |
| Epithelium | 2+ | 3+ | Fetal membranes | | |
| Musculature | 1+ | 1+ | Amniotic epithelium | 3+ | 2+ |
| Vascular endothelium | 2+ | 2+ | Decidual cells | 3+ | 1+ |
| Deferent duct | | | Fibroblasts | 3+ | |
| Epithelium | 2+ | 3+ | Cervix uteri | | |
| Longitudinal muscle layer | 0 | +/− | Glandular epithelium 0 | 0 | |
| Annular muscle layer | 2+ | 3+ | Vascular endothelium | 1+ | 0 − 1 |
| Vascular endothelium | 2+ | 3+ | Stroma | 1+ | 0 − 1 |
| Prostate | | | Fallopian tube | | |
| Glandular epithelium | 2+ | 2+ | Epithelium | 2+ | 3+ |
| Musculature | 1+ | 1+ | Musculature | 0 | 1+ |
| Vascular endothelium | 1+ − 2+ | 1+ − 2+ | Vascular endothelium | 1+ | 2+ |
| Kidney | | | Breast | | |
| Tubules | 2+ | 1+ | Epithelia mammary gland lobules | 2+ | 2+ |
| Glomerules | 0 | 0 | Duct epithelium 2+ secretory ducts | 2+ | |
| Medullary epithelium | 1+ | 1+ | Fibroblasts | 0 | 1+ |
| Vascular endothelium | 0 − 1+ | 0 − 1+ | Plasma cells | 2+2+ | |
| Bladder | | | Vascular endothelium | 1+ | 0 |
| Urothelium | 2+ | 1+ − 2+ | Thyroid | | |
| Musculature | 2+ | 1+ | Follicular epithelium | 2+ | |
| Plasma cells | 2+ | 2+ | Stroma | 1+ | 1+ |
| Fibroblasts | 1+ − 2+ | 1+ − 2+ | Vascular endothelium | 1+ | 0 |
| Peripheral nerve | | 0 | Thymus | | |
| Adrenal gland | | | Hassall's bodies | 2+ − 3+ | 2+ |
| Glomerular zone | 2+ | 1+ | Follicles | 1+ | 2+ |
| Fascicular zone | 1+ − 2+ | (1+) | Mantle zone | (1+) | (1+) |
| Reticular zone | 3+ | (1+) | Starry sky macrophages | 1+ | 1+ |
| Medulla | 0 | 0 | Spleen ++ | | |
| Vascular endothelium | 1+ | (1+) | Tonsils | +/− | +/− |
| Endometrium | | | Lymph nodes | +/− | +/− |
| Glandular epithelium | 3+ | 2+ | Maxillary sinus | | |
| Stroma cells | 0 | 1+ | Respiratory epithelium | 2+ | 2+ |
| Myometrium | 1+ | 1+ | Plasma cells | 3+ | 3+ |
| Vascular endothelium | 1+ | 2+ | Vascular endothelium | 1+ | 1+ |
| Lung | | | Fatty tissue | 2+ | 2+ |
| Bronchial epithelium | 2+ | 1+ | Vascular endothelium | 2+ | 2+ |
| Alveolar epithelium | 1+ − 2+ | 1+ | Skin | | |
| Bronchial glands | 1+ | 1+ | Epidermis | 2+ | 1+ − 2+ |
| Cartilage | 3+ | 1+ | Dermis | (1+) | 0 |
| Musculature | 1+ | 1+ | Hypodermis | (1+) | 0 |
| Alveolar macrophages | 2+ | 2+ | Sweat glands | 1+ | 0 |
| Elastic fibers | 2+ − 3+ | 2+ − 3+ | Vascular endothelium | 1+ | 0 |
| Vascular endothelium | 1+ | 1+ | Endocardium | 0 | 0 |
| Skeletal muscles | 2+ | 1+ | Fibroblasts | 2+ − 3+ | 2+ − 3+ |

0 = negative
1+ = weakly positive
2+ = moderately strong positive
3+ = strongly positive Endocrine cells such as the islets of Langerhans of the pancreas, the Leydig cells of the testicular interstitium, the decidual cells of the placenta, the oxyntic gland body of the stomach cardia, and the highly cylindrical epithelium of the cystic duct, display a strong reaction, which in part, shows fine granules. Strongly positive reactions were observed in plasma cells located in tissue structures and ganglionic cells and nerve cells of the cortex. The decidual cells, the amniotic epithelium and the fibroblasts of fetal membranes displayed very strong immunohistological stainability, as did the epithelium lining the seminal glands and the enterocytes of the small intestine.

Studies of formalin-fixed, paraffin-embedded tumor material of urological tumors displayed a weak to moderately strong intracytoplasmatical reaction of different differentiated adenocarcinomas of the prostate. Tumor cells of seminomatous testicular tumors showed only a weak intracytoplasmatic reaction while non-seminomatous tumors (embryonic carcinomas and chorionic carcinomas) had a widely increased stainability of the tumor cells, indicating increased concentrations of FSAP.

The diagnostic method of the invention thus allows an immunohistochemical detection of pathological processes in a wide variety of organs.

EXAMPLE II BRUNECK STUDY

Study Subjects

The Bruneck study is a prospective population study aimed at throwing light on epidemiology and etiology of carotid atherosclerosis (1–6). The study population was recruited in 1990 as a sample stratified according to sex and age and all the Bruneck inhabitants from 40 to 79 years of age (125 women and 125 men from each of decades 5 to 8 of age, n=1000). In total, 93.6% took part, with 919 completing the data acquisition. During the follow-up period between summer 1990 and 1995 (quinquennium$_1$—Q$_1$), a subgroup of 62 individuals died, while one subject moved house. Follow-up in the remaining population was 96.5% complete (n=826) (1–3). Before entry in the study, all the participants gave their consent after they had been informed about the study. As part of the follow-up in 1995, blood samples were taken to obtain DNA. Unsatisfactory PCR products were obtained in 16 cases, i.e. 810 men and women remained for the main analysis. Of these subjects, 94 died between summer 1995 and 2000 (quinquennium$_2$—Q$_2$). A total of 675 subjects underwent ultrasound investigation again in 2000 (follow-up rate among the survivors 94.3%) (6).

Clinical History and Examination

The study protocol included a clinical examination with priority for cardiological and neurological items and standardized questionnaires concerning the current or past vulnerability due to potential vascular risk factors (3–5). For smokers and former smokers, the average number of cigarettes smoked each day, and the pack-years, were recorded. The alcohol consumption was quantified as grams per day and classified in four categories (3). Systolic and diastolic blood pressures were the means of three measurements, in each case measured after resting for $\geq 10$ minutes. Hypertension was defined as a blood pressure of $\geq 160/95$ or intake of antihypertensive agents (WHO definition). A standardized oral glucose tolerance test was carried out on all subjects excepting those previously known to be diabetic. Diabetes mellitus was entered as present for those subjects whose fasting blood glucose level was $\geq 140$ mg/dl (7.8 mmol) and/or who had a 2-hour level (oral glucose tolerance test) of $\geq 200$ mg/dl (11.0 mmol/l).

Laboratory Methods

After the subjects had taken no food and not smoked for at least 12 hours, blood was taken from the antecubital vein (3–6). Total cholesterol and cholesterol with high density lipoprotein were determined enzymatically (CHOD-PAP method, Merck, Darmstadt, Germany), and lipoprotein(a) concentrations were measured using an ELISA (Immuno, Vienna, Austria). The cholesterol with low density lipoprotein was calculated from the Freidewald formula. Fibrinogen was measured by the method of Clauss, and the antithrombin III using a chromogenic assay. The Leiden mutation of factor V was detected by allele-specific PCR amplification (3).

FSAP antigen concentrations and scuPA-activating effect were determined as described recently (7, 8). Stated briefly, an ELISA with monoclonal antibodies (mAb) against FSAP was used for antigen quantification. The activity assay comprised an immunoadsorption onto microtiter plates coated with antibodies, a washing step and subsequent activation of prourokinase by FSAP, which was quantified by photometric observation of the amidolysis of a chromogenic substrate for urokinase. Pooled plasma from more than 200 healthy blood donors was used as arbitrary standard for both assays. A plasma equivalent unit (PEU) was defined as the FSAP antigenic activity present in one milliliter of the pooled plasma, which corresponds on average to 12 µg/ml (8).

DNA extraction and FSAP genotyping: high-quality DNA was obtained from frozen whole blood using a GenomicPrep Blood DNA Isolation Kit (Amersham Pharmacia Biotech). Ten ml of extracted DNA were amplified in 100 µl of 1×PCR standard reaction buffer with 50 pmol of the corresponding exon-specific forward and reverse primer, 1.5 mM MgCl$_2$, 0.2 mM dNTP and 2.5 units of Taq DNA polymerase (Perkin Elmer, Langen, Germany); an initial 2-minute denaturation at 94° C. was followed by 35 thermocycles each for 30 seconds at 94° C., 30 seconds at 50° C. and 40 seconds at 72° C., which was followed by a final elongation step at 72° C. for 5 minutes. The pairs of primers used have recently been described in Roemisch J., Feussner A., Nerlich C., et al. The frequent Marburg I polymorphism impairs the prourokinase activating potency of the factor VII-activating protease. *Blood Coag Fibrinol* 2002; 13:1–9, which is incorporated herein by reference.

Scanning Protocol and Definition of the Ultrasound Endpoints

In the ultrasound examination, the internal carotid artery (bulbous and distal sections) and common carotid artery (proximal and distal sections) on both sides were scanned using a 10 MHz probe and a 5 MHz doppler (1,2). Atherosclerotic lesions were defined by two ultrasound criteria: 1) wall surface (protrusion into the lumen) and 2) wall texture (echogenicity). The maximum axial diameter of plaques was determined in each of 16 vessel sections (intra-observation coefficient of variation 10% or 15% depending on the vessel section). The thickness of the intima media was measured at the far walls of the common carotid artery (intra-observation coefficient of variation 7.9% (n=100)) (2). The scans were performed in 1990, 1995 and 2000 by the same experienced ultrasonic specialist, the clinical findings and laboratory values of the subjects being unknown to the ultrasonic specialist.

The development of atherosclerosis was characterized by the appearance of new plaques in previously normal sections. Thresholds of 0.7 mm (common carotid artery) and 1.0 mm (internal carotid artery) were introduced as minimum requirements concerning the plaque diameters in the definition of developing atherosclerosis, because smaller lesions were difficult to distinguish from focal/diffuse wall thickenings (1). Progression of non-stenotic lesions was defined as a relative enlargement of the plaque diameter of more than twice the measurement error of the method (1). In the current analysis, both processes were combined to a single result category referred to as "early atherogenesis" for easier presentation and because of the fact that most of the described risk factors were common to these processes. An "advanced atherogenesis" was assumed whenever the criterion of progression was met and the lumen was narrowed by >40%. As described elsewhere (1–5), the cutoff at 40% appeared to correspond to a biological threshold in our population, at which marked changes in the growth kinetics of plaques (continuous, slow and diffuse growth versus occasional and focal expansions of prominent lesions), in the risk profiles (conventional risk factors versus procoagulation risk factors) and in the process of vascular renewal (compensating or overcompensating versus insufficient or even absent) occurred, indicating a switch in the underlying pathogenetic mechanisms from conventional atherogenesis to atherothrombosis.

The reproducibility of the ultrasound categories was "nearly perfect" (kappa coefficients of >0.8, obtained from two independent measurements carried out by the same ultrasound specialist in a reproducibility sample of n=100 (1–3).

Statistical Analysis

Possible associations between FSAP mutations and the various stages of atherogenesis were examined by means of logistic regression analysis. A base model was adjusted only in relation to age and sex. Multivariate equations were fitted by a stepwise progressive selection procedure as already described (p values for entry and exclusion 0.10 and 0.15 respectively) (3, 10). Age and sex were additionally inserted into these models in order to take account of the age and sex structure of the population sample. The main analysis was concentrated on the period between 1990 and 1995 ($Q_1$). Analysis of advanced atherogenesis was restricted to subjects already suffering from atherosclerosis at the start of the study (n=326).

The regression-standardized atherogenesis risks were calculated for a number of risk factors. The marginal method of the regression adjustment procedure was used, because it is not based on the rare-disease assumption (11).

Results

In the Bruneck study cohort (n=810), 36 subjects were heterozygous for the Marburg I mutant of FSAP (17 men and 20 women) and one subject was homozygous, corresponding to an overall carrier rate [95% CI] in the general population of 4.4% [3.0% to 5.8%]. A cosegregation of the Marburg II mutant (E393Q) of FSAP was observed in 16 of the 37 individuals (43 percent, 8 men and 8 women), while the Marburg I mutant occurred in isolation in the remaining 21 subjects (57 percent, 9 men and 12 women).

Plasma samples from the subpopulation (n=82) were investigated for FSAP antigen concentrations and corresponding prourokinase-activating effects. In 76 subjects with wild-type FSAP, the average (±2×SD) antigen concentrations, activity concentrations and activity/antigen ratios were respectively 0.991 (0.552 to 1.430) PEU/ml, 1.036 (0.614 to 1.458) PEU/ml and 1.07 (0.63 to 1.51). In contrast thereto, all six carriers of the Marburg I mutant in this subgroup showed a distinctly reduced in vitro capacity to activate prourokinase (<0.150 to 0.626) and activity/antigen ratios of 0.38 to 0.58. There was hardly any overlap in the distribution of these parameters in the two genetic groups.

During the five-year follow-up period between 1990 and 1995 ($Q_1$), a total of 384 of the 810 subjects in the study (47.4%) developed new atherosclerotic lesions or showed extension of nonstenotic lesions (early atherogenesis), and 92 of 326 individuals (28.2%) with pre-existing plaques showed stenotic transformations (advanced atherogenesis). As expected, no relation was found between Marburg I mutant and early atherogenesis (age/sex adjusted, multivariate odds ratios [95% CI] of 0.6 [0.3 to 1.4] and 0.7 [0.3 to 1.7]. Consistent with this, there were no differences in the thickness of the intima media of the common carotid artery between the carriers of wild-type FSAP (0.95 mm) and of the Marburg I mutant of FSAP (0.94 mm; P=0.853 for the difference). However, it emerged that the mutant is a strong risk factor for the advanced putative atherothrombotic stage in atherogenesis (age/sex adjusted odds ratio [95% CI] 3.5 [1.1 to 11.4], P=0.036). The association remained statistically significant on adjustment of the logistic regression model for other relevant risk factors (tab. 1). The risk profile for advanced stenotic atherosclerosis also included diabetes, a high fibrinogen concentration, a low antithrombin concentration, a high platelet count, smoking, alcohol consumption (small amounts protective), Lp(a)>0.32 g/l and Leiden mutation of factor V. There were no sex-specific differences in the risk factors, and no evidence of differential effects of the Marburg I mutant was found in subpopulations arranged according to age, level of risk and life style. Exclusion of subjects taking aspirin, antihypertensive agents, antidiabetics or lipid-lowering agents likewise did not affect the results. Regression-standardized risks of advanced atherogenesis for a number of major risk factors (Marburg I mutant, IGT/diabetes, high lipoprotein(a) concentration, smoking, factor V mutation, high fibrinogen concentration and low antithrombin concentration) are shown in table 2. Subjects with none of the risk factors had a low risk for development/progression of carotid stenosis, whereas subjects with a cluster of more than two factors almost obligatorily experienced advanced atherogenesis.

The Marburg II mutant had no effect on in vitro activation of single-chain plasminogen activators by FSAP. Accordingly, it was not unexpected that no association between this mutation and atherogenesis could be found in our analyses. On comparison of subjects with wild-type FSAP and carriers of the Marburg II mutant, of the Marburg I mutant and carriers of both genetic deviations, the multivariate odds ratios [95% CI] for advanced atherosclerosis were 1.6 [02 to 13.7], P=0.669, 6.2 [1.1 to 36.0], P=0.048 and 7.1 [1.1 to 45.1], P=0.037.

To demonstrate that our findings are also consistent over longer periods, the calculations were repeated with the data from the ten-year follow-up period between 1990 and 2000 ($Q_{1+2}$). In these equations, the multivariate relation between the Marburg I mutant of FSAP and advanced atherosclerosis (same adjustments as for the original analysis) was again statistically significant (multivariate odds ratio [95% CI] 4.1 [1.1 to 14.8], P=0.045).

TABLE 5

Multivariate logistic regression analysis of advanced atherogenesis according to age, sex, Marburg I mutant of FSAP and other potential vascular risk factors.

| | Means ± standard deviation (%) | | | | |
| --- | --- | --- | --- | --- | --- |
| Variable | AS−<br>(n = 234) | AS+<br>(n = 92) | Odds ratio<br>(95% CI) | P value | Step |
| Age, y | 64.9 ± 9.2 | 67.8 ± 8.0 | 1.87(1.19 – 2.92) | .0064 | 0 |
| Female sex | 109(46.6%) | 32(34.8%) | 0.56(0.25 – 1.25) | .1555 | 0 |
| Glucose tolerance | | | | <.0001 | 1 |
| IGT | 20(8.5%) | 16(17.4%) | 3.31(1.37 – 7.99) | .0081 | |
| DM | 10(8.1%) | 21(22.8%) | 6.38(2.71 – 14.99) | <.0001 | |
| Cigarettes/day | 3.2 ± 7.2 | 6.6 ± 9.6 | 1.77(1.30 – 2.40) | .0003 | 2 |
| Lp(a) > 0.32 g/l | 36(15.4%) | 25(27.2%) | 4.06(1.83 – 8.96) | .0005 | 3 |
| Alcohol consumption | | | | .0043 | 4 |
| <1 g/d | 114(48.7%) | 42(45.6%) | 1.00 | | |
| 1–50 g/d | 60(25.7%) | 15(16.3%) | 0.26(0.10 – 0.66) | .0046 | |
| 51–99 g/d | 37(15.8%) | 17(18.5%) | 1.03(0.40 – 2.70) | .9475 | |
| ≧100 g/d | 23(9.8%) | 18(19.6%) | 1.90(0.63 – 5.69) | .2535 | |
| Fibrinogen, g/l | 2.7 ± 0.6 | 2.9 ± 0.6 | 1.53(1.12 – 2.09) | .0083 | 5 |
| Marburg I FSAP mutation | 5(2.1%) | 8(8.7%) | 6.63(1.58 – 27.72) | .0099 | 6 |
| Factor V mutation | 5(2.1%) | 7(7.6%) | 4.70(1.19 – 18.55) | .0291 | 7 |
| Antithrombin III, % | 96.3 ± 13.0 | 92.8 ± 16.4 | 0.74(0.55 – 1.00) | .0500 | 8 |
| Platelet count, × $10^9$/l | 217.4 ± 56.5 | 230.3 ± 56.6 | 1.32(0.98 – 1.77) | .0769 | 9 |

Odds ratios (OR), 95% confidence interval (95% CI) and p values (P) were derived from the logistic regression analysis of advanced atherosclerosis (development/progression of stenotic carotid atherosclerosis) in relation to age, sex and vascular risk factors. The model was fitted by a stepwise progressive selection process (step . . . entry step). The ORs were calculated for a 1-SD unit change of given variables.

AS−: group without advanced atherogenesis, AS+: group with advanced atherogenesis. This analysis was concentrated on the 326 subjects who already suffered from atherosclerosis at the start of the study in 1990.

REFERENCES

1. Kiechl S, Willeit J. The natural course of atherosclerosis. Part I: incidence and progression. *Arterioscler Thromb Vasc Biol* 1999; 19: 1480–90.

2. Kiechl S, Willeit J. The natural course of atherosclerosis. Part II: vascular remodeling. *Arterioscler Thromb Vasc Biol* 1999; 19: 1491–8.

3. Willeit J, Kiechl S, Oberhollenzer F, et al. Distinct risk profiles of early and advanced atherosclerosis. Prospective results from the Bruneck Study. *Arterioscler Thromb Vasc Biol* 2000; 20: 529–37.

4. Kiechl S, Egger G, Mayr M, et al. Chronic infections and the risk of carotid atherosclerosis. Prospective results from a large population study. *Circulation* 2001; 103: 1064–70.

5. Kiechl S, Willeit J, Egger G, Poewe W, Oberhollenzer F. Body iron stores and the risk of carotid atherosclerosis. Prospective results from the Bruneck Study. *Circulation* 1997; 96: 3300–7.

6. Kiechl S, Lorenz E, Reindl M, Wiedermann C J, Oberhollenzer F, Bonora E, Willeit J, Schwartz D A. Toll-like receptor 4 polymorphisms and atherogenesis in humans. *N Engl J Med* 2002; 347: 185–92.

7. Roemisch J, Feussner A, Stohr H A. Quantification of the factor VII- and single-chain plasminogen activator-activating protease in plasmas of healthy subjects. *Blood Coagul. Fibrinolysis.* 2001; 12: 375–83.

8. Kannemeier C, Feussner A, Stohr H A, Weisse J, Preissner K T, Roemisch J. Factor VII and single-chain plasminogen activator-activating protease: activation and autoactivation of the proenzyme. *Eur J Biochem.* 2001; 268: 3789–96.

9. Roemisch J, Feussner A, Nerlich C, Stoehr H A, Weimer T. The frequent Marburg I polymorphism impairs the prourokinase activating potency of the factor VII-activating protease (FSAP). *Blood Coag Fibrinol* 2002; 13: 1–9.

10. Hosmer D W, Lemeshow S. *Applied Logistic Regression.* New York: John Wiley & Sons, 1988.

11. Wilcosky T C, Chambless L E. A comparison of direct adjustment and regression adjustment of epidemiological measures. *J. Chron Dis* 1985; 38: 849–56.

Figure Legend

FIG. 1 shows the regression-adjusted risk of advanced atherogenesis as a function of the vascular risk factors present in an individual (Marburg I mutant of factor VII-activating protease, IGT/diabetes, lipoprotein(a) concentration >0.32 g/l, smoking, Leiden mutation of factor V, fibrinogen concentration ($Q_5$, >3.2 g/l) and antithrombin concentration ($Q_1$, <84%)).

What is claimed is:

1. An isolated coagulation factor VII-activating protease (FSAP) mutant derived from a human donor, which is an atherothrombosis risk factor, and which comprises a Gly to Glu exchange at amino acid position 534 of the FSAP proenzyme sequence, said amino acid sequence position defined according to the proenzyme amino acid sequence of SEQ ID NO:5.

2. The risk factor as claimed in claim 1, wherein the FSAP mutant further comprises a Glu to Gln exchange at amino acid position 393 of the proenzyme sequence, said amino acid sequence position defined according to the proenzyme amino acid sequence of SEQ ID NO:5.

3. The risk factor as claimed in claim 1, wherein the FSAP mutant is encoded by a proenzyme nucleotide sequence comprising a G to A base exchange at position 1601, said nucleotide sequence position defined according to the proenzyme nucleotide sequence of SEQ ID NO:1.

4. The risk factor as claimed in claim 3, wherein the FSAP mutant is encoded by a proenzyme nucleotide sequence further comprising a G to C base exchange at position 1177, said nucleotide sequence position defined according to the proenzyme nucleotide sequence of SEQ ID NO:1.

5. The risk factor as claimed in claim 1, wherein the FSAP mutant has partially or completely lost the ability to activate single-chain plasminogen activators, as compared with wild-type FSAP.

6. The risk factor as claimed in claim 1, wherein the FSAP mutant has partially or completely lost the ability to activate prourokinase, as compared with wild-type FSAP.

7. The risk factor as claimed in claim 1, which indicates a genetic predisposition to the development of atherosclerotic disorders and their sequelae, or thrombotic disorders and their sequelae.

8. The risk factor as claimed in claim 7, which indicates a genetic predisposition to the development of at least one of arterial and venous occlusive disorders.

9. The risk factor as claimed in claim 7, which indicates a genetic predisposition to the development of at least one of atherosclerotic and thrombotic restrictions of organ functions.

10. The risk factor as claimed in claim 7, which indicates a genetic predisposition to the development of one or more of angina pectoris, myocardial infarction, and strokes.

11. The atherothrombosis risk factor as claimed in claim 1, wherein the ability to activate single-chain plasminogen activators, measured in at least one of whole blood and blood plasma, is reduced as compared with wild-type FSAP.

12. The atherothrombosis risk factor as claimed in claim 1, wherein the ability to activate prourokinase, measured in at least one of whole blood and blood plasma, is reduced as compared with wild-type FSAP.

13. A diagnostic method for identifying the atherothrombosis risk factor as claimed in claim 1, which comprises:

(a) determining FSAP prourokinase activating activity in one or more body fluids of an individual;

(b) comparing said FSAP prourokinase activating activity in one or more body fluids of an individual to FSAP prourokinase activating activity in a standard comprising wild-type FSAP;

(c) identifying a reduced FSAP prourokinase activating activity in said one or more body fluids of the individual compared to the FSAP prourokinase activating activity in said standard; and (d) analyzing at least one of genomic DNA, mRNA, or cDNA of the individual with the reduced FSAP prourokinase activating activity to detect the presence of a heterozygous or homozygous mutation in the FSAP nucleotide sequence, said mutation comprising a G to A base exchange at nucleotide position 1601, said nucleotide sequence position defined according to the proenzyme nucleotide wherein the presence of said mutation identifies the atherothrombosis risk factor sequence of SEQ ID NO:1.

14. The diagnostic method as claimed in claim 13, further comprising determining the FSAP protein concentration in said one or more body fluids of the individual, and calculating the ratio between said FSAP protein concentration and FSAP prourokinase activating activity in said one or more body fluids.

15. The diagnostic method as claimed in claim 13, wherein the one or more body fluids comprise blood plasma.

16. The diagnostic method as claimed in claim 13, further comprising determining the activation of single-chain tissue plasminogen activators in one or more body fluids of the individual.

17. The diagnostic method as claimed in claim 13, further comprising analyzing at least one of the genomic DNA, mRNA, or cDNA of the individual to detect the presence of a heterozygous or homozygous mutation in the FSAP nucleotide sequence, said mutation comprising a G to C base exchange at nucleotide position 1177, said nucleotide sequence position defined according to the proenzyme nucleotide sequence of SEQ ID NO:1.

18. The diagnostic method as claimed in claim 13, wherein the FSAP prourokinase activating activity is measured by:

(a) incubating said one or more body fluids of the individual on a solid support to immobilize FSAP on said solid support;

(b) washing the support; and (c) incubating the FSAP immobilized on the support with reagents which allow determination of the prourokinase activating activity of the FSAP immobilized on the support.

19. The risk factor as claimed in claim 3, wherein the FSAP mutant is encoded by a proenzyme nucleotide sequence further comprising a base exchange at position 183 which does not lead to an amino acid exchange, said nucleotide sequence position defined according to the proenzyme nucleotide sequence of SEQ ID NO:1.

20. The risk factor as claimed in claim 3, wherein the FSAP mutant is encoded by a proenzyme nucleotide sequence further comprising a base exchange at position 957 which does not lead to an amino acid exchange, said nucleotide sequence position defined according to the proenzyme nucleotide sequence of SEQ ID NO:1.

* * * * *